United States Patent [19]

Moriwaki et al.

[11] Patent Number: 4,960,770
[45] Date of Patent: Oct. 2, 1990

[54] 2-ALKYL THIENO(TRIAZOLO)DIAZEPINE COMPOUNDS AND PHARMACEUTICAL USES THEREOF

[75] Inventors: Minoru Moriwaki, Nakatsu; Masao Abe, Buzen; Hiroshi Mikashima, Fukuoka; Tetsuya Tahara, Nakatsu, all of Japan

[73] Assignee: Yoshitomi Pharmaceutical Industries, Ltd., Osaka, Japan

[21] Appl. No.: 304,989

[22] PCT Filed: May 25, 1988

[86] PCT No.: PCT/JP88/00506

§ 371 Date: Jan. 11, 1989

§ 102(e) Date: Jan. 11, 1989

[87] PCT Pub. No.: WO88/09333

PCT Pub. Date: Dec. 1, 1988

[30] Foreign Application Priority Data

May 28, 1987 [JP] Japan .................................. 62-132058
May 29, 1987 [JP] Japan .................................. 62-137195
Jun. 16, 1987 [JP] Japan .................................. 62-149698

[51] Int. Cl.$^5$ ...................... A61K 31/55; C07D 243/24
[52] U.S. Cl. ..................................... 514/219; 514/220; 540/564
[58] Field of Search .................. 540/564; 514/220, 219

[56] References Cited

FOREIGN PATENT DOCUMENTS 0176927 4/1986 European Pat. Off. ............ 514/220

OTHER PUBLICATIONS

Merck Index, 11th Ed., (Merck and Co., Rahway, N.J., 1989), Manologe No. 3830, p. 608.

*Primary Examiner*—Mukund J. Shah
*Assistant Examiner*—E. C. Ward
*Attorney, Agent, or Firm*—Wenderoth, Lind & Ponack

[57] ABSTRACT

A thienotriazolodiazepine compound of the formula:

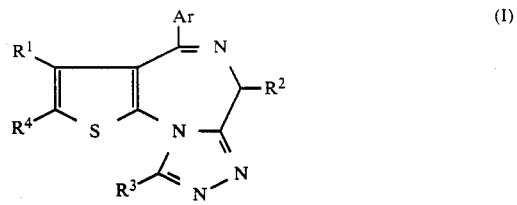

wherein Ar is phenyl, pyridyl, substituted phenyl or substituted pyridyl; $R^1$ and $R^3$ are the same or different and each is hydrogen, alkyl having 1 to 4 carbon atoms; $R^2$ is hydrogen, alkyl having 1 to 4 carbon atoms or trifluoromethyl; $R^4$ is straight or branched chain alkyl, alkenyl or alkynyl having 6 to 18 carbon atoms, or a thienodiazepine compound of the formula:

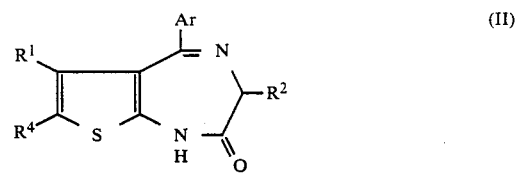

wherein Ar, $R^1$, $R^2$ and $R^4$ are as defined above, and pharmaceutically acceptable acid addition salt thereof.

These compounds are useful as drugs for the treatment of circulatory diseases and various PAF-induced diseases. The compound (II) is also useful as an intermediate for preparing the compound (I).

5 Claims, No Drawings

2-ALKYL THIENO(TRIAZOLO)DIAZEPINE COMPOUNDS AND PHARMACEUTICAL USES THEREOF

TECHNICAL FIELD

The present invention relates to pharmaceutically useful and novel thieno(triazolo)diazepine compounds which have coronary vasodilating activity, vertebral blood flow increasing activity, calmodulin inhibitory activity, calcium/calmodulin dependent phosphodiesterase inhibitory activity, red cell deformability improving activity and/or antagonistic activity on platelet activating factor (hereinunder referred to as PAF), and pharmaceutically acceptable acid addition salts thereof, and pharmaceutical uses thereof.

BACKGROUND ART

Japanese Patent Application Publication (Kokoku) Nos. 49-40000 and 49-40238 disclose that certain thieno[2,3-e]1,4-diazepine derivatives possess activities against the central nervous system such as antianxiety or anticonvulsant activities, and Japanese Patent Application Publication (Kokai) No. 61-87623 discloses that the similar compounds exhibit antagonistic activity on PAF.

Furthermore, certain thienotriazolodiazepine compounds are known to exhibit activities against the central nervous system such as antianxiety or anticonvulsant activities as disclosed in, for example, Arzneim. Forsch. (Drug Res.) Vol. 28(II), p. 1165 (1978). Japanese Patent Application Publication (Kokai) No. 61-87684 and so on also disclose that the similar kinds of compounds possess antagonistic activity on PAF.

However, the several kinds of compounds explicitly disclosed in the column of pharmacological experiments of the above Japanese Patent Application Publication (Kokai) No. 61-87684 are not desirable as drugs for treatment of various PAF-induced diseases because they have excellent antianxiety activities and their activities against the central nervous system are very potent. Therefore, it has been desired to provide more useful compounds in view of the separation from the effect on the central nervous system, the reinforcement of antagonistic activity on PAF, the manifestation of activity by oral administration or the duration of activity.

It is also recognized that research and development of effective drugs against various circulatory diseases are matter of urgent necessity because of the recent increase of mortality caused by such diseases However, these preceding thienotriazolodiazepine compounds are not known to exhibit useful direct activity on circulatory systems except antagonistic activity on PAF-induced action.

DISCLOSURE OF INVENTION

The present inventors have made intensive investigations in order to develop compounds which exhibit less activity against the central nervous system, but which possess potent antagonistic activity on PAF show also effectiveness by oral administration and long-lasting, and furthermore other useful activities. As a result of such investigations, the present inventors have surprisingly found that certain thienotriazolodiazepine compounds and thienodiazepine compounds, starting materials thereof, which are not definitely disclosed in the above Japanese Patent Application Publication (Kokai) No. 61-87684 possess potent coronary vasodilating activity, vertebral blood flow increasing activity, calmodulin inhibitory activity, calcium/calmodulin dependent phosphodiesterase inhibitory activity and red cell deformability improving activity and are useful for the treatment of heart failure, ischemic heart disease, cerebral circulatory disturbance or various diseases induced by them. Furthermore, the present inventors have found that the compounds exhibit excellent antagonistic activity on PAF compared to those preceeding compounds and substantially have no activity against the central nervous system and are also effective by oral administration and long-lasting, and completed the present invention.

The present invention relates to
(1) a thienotriazolodiazepine compound of the formula:

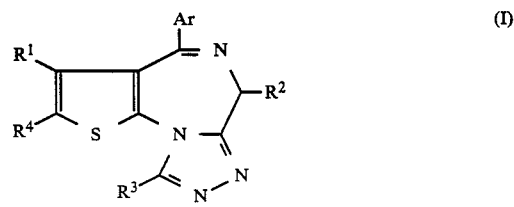

(I)

wherein Ar is phenyl, pyridyl, substituted phenyl or substituted pyridyl; $R^1$ and $R^3$ are the same or different and each is hydrogen, alkyl having 1 to 4 carbon atoms; $R^2$ is hydrogen, alkyl having 1 to 4 carbon atoms or trifluoromethyl; $R^4$ is straight or branched chain alkyl, alkenyl or alkynyl having 6 to 18 carbon atoms, or a pharmaceutically acceptable acid addition salt thereof,
(2) a thienodiazepine compound of the formula:

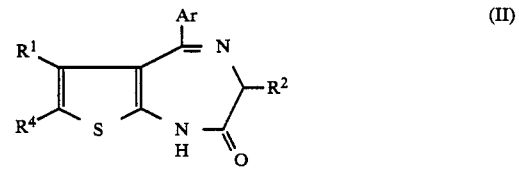

(II)

wherein Ar, $R^1$, $R^2$ and $R^4$ are as defined above, or a pharmaceutically acceptable acid addition salt thereof,
(3) a drug for treatment of circulatory diseases comprising a compound of the formula (I) or (II) or a pharmaceutically acceptable acid addition salt thereof as an effective ingredient, (4) a drug for treatment of circulatory diseases as mentioned above (3) which is a coronary vasodilating agent, a drug for heart failure or a cerebral vasodilating agent, and (5) a drug for treatment of various diseases induced by platelet activating factor comprising a compound of the formula (I) or (II) or a pharmaceutically acceptable acid addition salt thereof as an effective ingredient.

The compounds of formula (II) are also important as an intermediate for preparing the compounds of formula (I).

In the above formulae, substituents of the substituted phenyl or substituted pyridyl in the symbol of Ar include the same or different 1 to 3 substituents such as halogen (e.g. chlorine, bromine or fluorine), lower alkyl (alkyl having 1 to 4 carbon atoms such as methyl, ethyl, propyl, isopropyl, butyl, isobutyl or tert-butyl) or lower alkoxy (alkoxy having 1 to 4 carbon atoms such as methoxy, ethoxy, propoxy, isopropoxy, butoxy, isobutoxy or tert-butoxy), or the adjacent two carbon atoms on Ar may optionally be substituted by alkylenedioxy such as methylenedioxy or ethylenedioxy.

Alkyl having 1 to 4 carbon atoms in the symbols of $R^1$, $R^2$ and $R^3$ includes, for example, methyl, ethyl, propyl, isopropyl, butyl, isobutyl or tert-butyl.

Straight or branched chain alkyl having 6 to 18 carbon atoms in the symbol of $R^4$ includes, for example, hexyl, heptyl, octyl, 2-ethylhexyl, decyl, dodecyl, tetradecyl, hexadecyl or octadecyl; straight or branched chain alkenyl having 6 to 18 carbon atoms includes, for example, 2-hexenyl, heptenyl, octenyl, 1,5-dimethyl-4-hexenyl, geranyl, octadecenyl or linolenyl; straight or branched chain alkynyl having 6 to 18 carbon atoms includes, for example, 3-hexynyl, heptynyl, 3-octynyl, dodecynyl or pentadecynyl.

The pharmaceutically acceptable acid addition salt of the compound of formula (I) or formula (II) includes, for example, salt with an inorganic acid such as hydrochloride, sulfate, phosphate, hydrobromide or nitrate or salt with an organic acid such as maleate, fumarate, malate, tartrate, succinate, citrate, acetate, lactate, methanesulfonate or p-toluenesulfonate.

The present invention embraces optical isomers, diastereoisomers and racemates thereof, for the compounds of the present invention having chiral carbon atom(s) and also includes position isomers.

The compounds of formula (I) of the present invention can be prepared by reacting a compound of formula (II) with a thionating agent and then reacting thus obtained compound of formula:

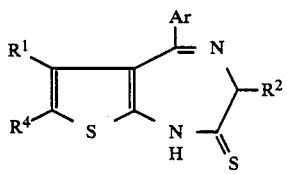
(III)

wherein Ar, $R^1$, $R^2$ and $R^4$ are as defined above, with a compound of the formula:

(VI)

wherein $R^3$ is as defined above, or the compounds of formula (I) can also be prepared by reacting the compound of formula (III) with hydrazine or hydrate thereof and then reacting the obtained compound of formula:

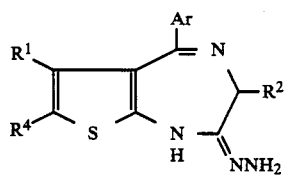
(V)

wherein Ar, $R^1$, $R^2$ and $R^4$ are as defined above, with a compound of the formula:

(VI)

wherein $R^3$ is as defined above, or a reactive derivative thereof, or with a compound of the formula:

(VII)

wherein $R^5$ is lower alkyl such as methyl, ethyl, propyl, isopropyl, butyl, isobutyl or tert-butyl, and $R^3$ is as defined above.

In the above reaction, thionating agent includes, for example, phosphorus pentasulfide and 2,4-bis(4-methoxyphenyl)-1,3,2,4-dithiadiphosphetan-2,4-disulfide (Lawesson reagent), and a reactive derivative of compound (VI) include, for example, a carboxylic acid halide (e.g. carboxylic acid chloride or carboxylic acid bromide), a carboxylic acid anhydride, a mixed acid anhydride (e.g. lower alkyl carbonate with mixed acid anhydride or mixed acid anhydride with alkyl phosphate), a lower alkyl ester (e.g. methyl ester or ethyl ester) and an active ester (e.g. benzyl ester, p-nitrobenzyl ester, p-nitrophenyl ester or p-chlorophenyl ester).

The reaction of the compound (II) with the thionating agent is usually carried out at 30°–100° C. in an inert solvent (e.g. pyridine, dimethylaniline, benzene, toluene, xylene, tetrahydrofuran, dioxane, chloroform or a mixed solvent thereof) for 30 minutes to 5 hours.

The reaction of the compound (III) with the compound (IV) is usually carried out at a temperature of from room temperature to the refluxing temperature of the employed solvent in an inert solvent (e.g. benzene, toluene, xylene, tetrahydrofuran, dioxane, methanol, ethanol, propanol, isopropyl alcohol or a mixed solvent thereof) in the presence of an organic acid (e.g. acetic acid or propionic acid), and inorganic acid (e.g. hydrochloric acid or sulfuric acid) or silica gel for 30 minutes to 5 hours.

The reaction of the compound (III) with hydrazine or hydrate thereof is usually carried out at 0°–40° C. in an inert solvent (e.g. methanol, ethanol, propanol, isopropyl alcohol or butanol) for 5 minutes to 3 hours.

The reaction of the compound (V) with the compound (VI) of reactive derivative thereof or the compound (VII) is usually carried out at a temperature of from room temperature to the refluxing temperature of the employed solvent in an inert solvent (e.g. benzene, toluene, xylene, tetrahydrofuran, dioxane or a mixed solvent thereof) in the presence of an organic acid (e.g. acetic acid or propionic acid), an inorganic acid (e.g. hydrochloric acid or sulfuric acid) or silica gel for 30 minutes to 6 hours.

The compounds of formula (I) can be isolated and purified from thus obtained resulting mixture by means of a known and conventional manner such as recrystallization or chromatography.

The compounds of formula (I) can be converted into the above-mentioned pharmaceutically acceptable salts by treating the compounds with inorganic or organic acids in a conventional manner.

Preferable compounds of the formula (I) are, for example, 4-(2-chlorophenyl)-2-hexyl-9-methyl-6H-thieno[3,2-f][1,2,4]triazolo[4,3-a][1,4]diazepine, 2-hexyl-4-(2-methylphenyl)-9-methyl-6H-thieno[3,2-f][1,2,4]triazolo[4,3-a][1,4]diazepine, 2-hexyl-4-(2-methoxyphenyl)-9-methyl-6H-thieno[3,2-f][1,2,4]triazolo 4,3-a][1,4]diazepine, 4-(2-chlorophenyl)-2-octyl-9-methyl-6H-thieno[3,2-f][1,2,4]triazolo[4,3-a]diazepine, 2-hexyl-4-(4-methylphenyl)-9-methyl-6H-thieno[3,2-f][1,2,4]triazolo[4,3-a][1,4]diazepine, 2-hexyl-4-(3-methylphenyl)-9-methyl-6H-thieno[3,2-f][1,2,4]triazolo[4,3-a][1,4]diazepine, 2-hexyl-4-(3,4,5-trimethoxyphenyl)-9-methyl-6H-thieno[3,2-f][1,2,4]triazolo[4,3-a][1,4]diazepine, 2-hexyl-4-(2,5-dimethylphenyl)-9-methyl-6H-thieno[3,2-f][1,2,4]triazolo[4,3-a][1,4]diazepine, 4-(2-chlorophenyl)-2-hexyl-6,9-dimethyl-6H-thieno3,2-f][1,2,4]triazolo[4,3-a][1,4]diazepine, 2-hexyl-4-(2-methoxyphenyl)-6,9-dimethyl-6H-thieno[3,2-f][1,2,4]triazolo [4,3-a][1,4]diazepine and 2-hexyl-4-(2-methylphenyl)-6,9-dimethyl-6H-thieno[3,2-f][1,2,4]triazolo[4,3-a][1,4]diazepine.

Furthermore, the above-mentioned compound of formula (II) can be prepared, for example, by the following method. A compound of the formula:

ArCOCH$_2$CN  (VIII)

wherein Ar is as defined above, is reacted with a compound of the formula:

$$R^4CH_2CR^1 \atop \underset{O}{\|}$$  (IX)

wherein $R^1$ and $R^4$ are as defined above, at a room temperature or under heating in the presence of sulfur in a solvent such as an alcohol (e.g. methanol or ethanol), dimethylformamide or dimethylacetamide with a base catalyst such as triethylamine, pyrrolidine, piperidine or morpholine, and a resulting compound of the formula:

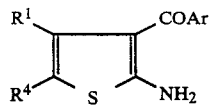
(X)

wherein Ar, $R^1$ and $R^4$ are as defined above, is reacted with a compound of the formula:

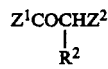
$$Z^1COCHZ^2 \atop R^2$$  (XI)

wherein $Z^1$ and $Z^2$ are the same or different and each is halogen such as chlorine or bromine, and $R^2$ is as defined above, and a N-haloacetyl compound thus obtained is reacted with potassium iodide or sodium iodide to convert to N-iodoacetyl compound, and then reacted with ammonia to give N-glycyl compound.

The reaction is carried out under cooling, at a room temperature or under heating in a solvent such as acetone, tetrahydrofuran or dioxane.

The compound (II) is prepared by subjecting thus obtained N-glycyl compound to ring closure reaction with dehydration at a room temperature or under heating in an inert solvent (e.g. ethanol, propanol, isopropyl alcohol, butanol, benzene, toluene, dimethylformamide or dimethylacetamide), preferably in the presence of a weak acid catalyst such as acetic acid, propionic acid or silica gel.

The compound of formula (II) can also be prepared by subjecting a compound of formula:

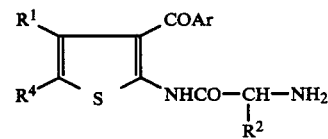
(XII)

wherein Ar, $R^1$, $R^2$ and $R^4$ are as defined above, to ring closure reaction with dehydration at a room temperature or under heating in an inert solvent (e.g. ethanol, propanol, isopropyl alcohol, butanol, benzene, toluene, dimethylformamide or dimethylacetamide), preferably in the presence of a weak acid catalyst such as acetic acid, propionic acid or silica gel.

In the above reaction, the compound of formula (XII) can be prepared by reacting the above-mentioned compound of formula (X) with a compound of the formula:

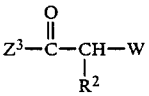
$$Z^3-\underset{\underset{R^2}{|}}{\overset{\overset{O}{\|}}{C}}-CH-W$$  (XIII)

wherein $Z^3$ is halogen such as chlorine or bromine, W is protected amine by protecting group and $R^2$ is as defined above, and then removing the protecting group of the thus obtained compound of formula:

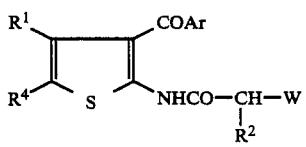
(XIV)

wherein Ar, $R^1$, $R^2$, $R^4$ and W are as defined above, according to a conventional manner.

In the compound of formula (XIII), the protected amine by protecting group which is represented by W means, for example, phthalimido, 2,3-diphenylmaleinimido or dithiasuccinimido, or protected amine by, for example, benzyloxycarbonyl, tert-butoxycarbonyl or formyl.

The compounds of formula (II) prepared by the above method can also be converted into the above-mentioned pharmaceutically acceptable salts by treating the compounds with inorganic or organic acids in a conventional manner.

The compounds (I), (II) of the present invention and pharmaceutically acceptable acid addition salts thereof possess coronary vasodilating activity, vertebral blood flow increasing activity, calmodulin inhibitory activity, calsium/ calmodulin dependent phosphodiesterase inhibitory activity and/or red cell deformability improving activity and also exhibit antagonistic activity on PAF, and these activities are long-lasting. Furthermore, they are low toxic and substantially exhibit no central depressant activity such as sedation nor muscle relaxant activity Therefore, the compounds (I) and (II) of the present invention and pharmaceutically acceptable acid addition salts thereof are useful as drugs of circulatory diseases, for example, as coronary vasodilator or cerebral vasodilator for treatment of heart failure, ischemic heart disease (e.g. angina pectoris or myocardial infraction) and cerebral circulatory disease (e.g. cerebral infarction, cerebral arteriosclerosis, cerebral hemorrhage or head injury) or diseases caused by them (e.g. loss of spontaneity, depression, or dysmnesia) and also are useful as drugs for treatment of various PAF-induced diseases (e.g. inflammatory disease, allergic disease, anaphylactic shock, myocardial disease, asthma, pulmonary edema or adult respiratory disease).

The thienodiazepine compound of formula (II) is also important as an intermediate for preparing the thienotriazolodiazepine compound of formula (I).

Pharmacological activities of the compounds of present invention are shown as follows.

Experiment 1: Effect on coronary flow

Adult mongrel dogs were anesthetized with sodium pentobarbital (30 mg/kg, i.v.). According to the method of Yago et al described in Folia Pharmacologica Japonica, vol. 57, p. 380 (1961), the left coronary artery was perfused and its blood flow was measured. Test compound was injected into the coronary artery at a volume of 10–30 μl. To determine the effect of the test compound on coronary artery blood flow, an increase percentage of blood flow at each dosage was calculated based on the increase of the blood flow at a dosage of 3 μg of nifedipine.

TABLE 1

| Test Compound | Effect on coronary blood flow (%) Dosage (μg): | | |
|---|---|---|---|
| (Example No.) | 30 | 100 | 300 |
| 58 | 63 | 107 | 136 |
| 61 | 55 | 69 | 103 |
| 67 | 43 | 86 | 114 |
| 68 | 33 | 63 | 100 |
| 74 | 16 | 57 | 86 |

Experiment 2: Inhibitory effect on platelet aggregation in rabbits (in vitro test)

Blood samples to which was added 0.1 volume of 3.8% sodium citrate were collected from rabbits. Platelet rich plasma (PRP) was prepared by centrifuging the blood sample at 200 x g for 10 minutes, and platelet poor plasma (PPP) was prepared by centrifuging the remaining blood sample at 1000 x g for 10 minutes.

Aggregation ability was measured with a turbidimetric device (6-channel NKK Hematracer 1, model PAT-6A) according to the method of G.V.R. Born described in J. Physiology, vol. 168, p. 178 (1963). The aggregometer was adjusted in sensitivity to give light transmission values of 0 and 100% for PRP and PPP, respectively. With stirring at 1000 rpm, 0.3 μl of test compound solution or vehicle was added to 0.3 ml of PRP. After the mixture was kept at 37° C. for 2 minutes, to the mixture was added 3 μl of synthesized platelet activating factor at the final concentration of $1.8 \times 10^{-7}$ M and the light transmission was recorded for 5 minutes.

The inhibition percentage of test compounds on platelet aggregation were calculated from the following formula by measuring the maximal light transmission in the presence and absence of the test compounds.

$$\% \text{ of inhibition} = \left(1 - \frac{\text{maximal aggregation in the presence of the test compound}}{\text{maximal aggregation in the absence of the test compound}}\right) \times 100$$

IC$_{50}$ (μg/ml, concentration of 50% inhibition) was graphically determined from the relation between the percentage of inhibition and dosage. The results were summarized in Table 2.

TABLE 2

| Test Compound (Example No.) | Inhibition of PAF-induced platelet aggregation, IC$_{50}$ (μg/ml) |
|---|---|
| 54 | 0.03–0.1 |
| 55 | 0.03–0.1 |
| 57 | 0.01–0.1 |
| 69 | 0.3–1 |
| 72 | 0.03–0.1 |
| 73 | 0.3–1 |

TABLE 2-continued

| Test Compound (Example No.) | Inhibition of PAF-induced platelet aggregation, IC$_{50}$ (μg/ml) |
|---|---|
| Etizolam | 1.3 |

In the table, Etizolam is a general name of 6-(o-chlorophenyl)-8-ethyl-1-methyl-4H-s-triazolo[3,4-c]thieno[2,3-e][1,4]diazepine.

Experiment 3: Inhibitory effect on platelet aggregation in rabbits (ex vivo test)

Test compound was orally administered to a group of three rabbits instead of adding it to PRP as in vitro test of Experiment 2, and then the citrated blood samples (1 volume of 3.8% sodium citrate +9 volumes of blood) were collected with the passage of time. Then, the blood samples were employed to determine the inhibitory effect according to Experiment 2. The results were summarized in Table 3.

TABLE 3

| Test Compound (Example No.) | Dose (mg/kg) p.o. | % of inhibition at each time after administration | | |
|---|---|---|---|---|
| | | 1 hour | 3 hours | 6 hours |
| 54 | 10 | 100 | 100 | 85 |
| Etizolam | 10 | | no effect | |

Experiment 4: Effect of PAF-induced lethal shock in mice

The experiment was carried out according to the method of Young et al. described in Prostaglandins, vol. 30, p. 545 (1985). Groups of 9 to 15 male ICR mice (Charles River) weighing 25–30 g were used. 80 μg/kg of PAF (Serdary Research Labo.) solution was intravenously administered in a lateral tail vein 1 hour after the oral administration of test compound (0.1 ml/10 g). All animals were observed for 24 hours after the PAF injection. Results were given as number of survivors/number of employed animals and survival rates (%) in Table 4.

TABLE 4

| Test Compound (Example No.) | Dose (mg/kg p.o.) | Number of Survivors Number of Animals | Survival rate (%) |
|---|---|---|---|
| 54 | 0.3 | 3/10 | 30 |
| | 3 | 10/10 | 100 |
| 61 | 1 | 6/8 | 75 |
| | 3 | 8/8 | 100 |
| 62 | 3 | 6/8 | 75 |
| 68 | 0.1 | 5/6 | 83.3 |
| | 0.3 | 6/7 | 85.7 |
| | 1 | 6/7 | 85.7 |
| 74 | 0.1 | 5/6 | 83.3 |
| | 1 | 7/7 | 100 |
| Controls | 0 | 0/15 | 0 |
| Etizolam | 1.0 | 1/11 | 9.1 |
| | 3.0 | 3/11 | 27.3 |
| | 10.0 | 6/11 | 54.5 |

Experiment 5: Effect of vertebral blood flow

Adult mongrel dogs were anesthetized with sodium pentobarbital (30 mg/kg. i.v.) and the blood flow of the left vertebral artery was measured. The effects of test compound on vertebral blood flow were expressed as ED$_{100}$ (μg), a dose required to obtain 100% of the blood flow increase by intraartery administration of 3 μg/kg of nifedipine. The results were given in the Table 5.

TABLE 5

| Test Compound (Example No.) | Effect on vertebral blood flow ED$_{100}$ (μg/kg, i.a.) |
| --- | --- |
| 65 | 99 |
| 67 | 78 |

Experiment 6: Calmodulin inhibitory action (NPN fluorescence probe method)

Calmodulin inhibitory action was measured according to the modified method of Epstein et al. described in Biochemical and Biophysical Research Communications, Vol. 105, p. 1142 (1982). Briefly, to 25 mM Tris-HCl buffer solution (pH 7.0) were added as a final concentration 1 mM calcium chloride, 5 μM N-phenyl-1-naphthylamine (NPN), 1000 units of calmodulin (bovine encephalon) and each of test compound to give 3 ml of final solution volume. The solution was allowed to stand at room temperature for 1 hour and the fluorescence intensity was measured by a fluorescene photometer (ex. 350 nm, em. 440 nm). A blank was prepared by adding water instead of calmodulin. Each of test compound was dissolved in dimethyl sulfoxide or 2.5% dimethyl sulfoxide solution and the final concentration of dimethyl sulfoxide was adjusted to 0.25%.

The results of measurement were represented as IC$_{50}$ value and shown in the Table 6.

TABLE 6

| Test Compound (Example No.) | Calmodulin inhibitory action IC$_{50}$ (μM) |
| --- | --- |
| 68 | 1.1 |
| 74 | 1.2 |

Experiment 7: Effect on calcium/calmodulin dependent phosphodiesterase

The experiment was carried out according to the method of Thompson et al. described in Advances in Cyclic Nucleotide Research, Vol. 10, p. 69 (1979). Briefly, the solution of which final volume was 200μl was prepared by mixing 40 μl of 200 mM Tris-HCl buffer solution (pH 8.0), containing 25 mM magnesium chloride and 0.5 mM ethyleneglycol-bis(β-aminoethylether)-N,N '-tetra acetic acid (EGTA), 20 μof 10μM [$^3$H]-cAMP (250 nCi), test compound and a solution of calcium/calmodulin dependent phosphodiesterase (PDE) enzyme. The test compound was dissolved in dimethyl sulfoxide to give 1% of final concentration. The incubation was performed at 37° C. for 20 minutes and then stopped by heating for 1 minutes in a boiling water bath. The resulting 5'-AMP was converted into adenosine by adding 50 μl of snake venom (1 mg/ml) and incubating at 30° C. for 10 minutes. Then, to the solution was added 500 μl of AGI-X8 (methanol:-resin=3:2) and the mixture was allowed to stand under ice-cooling for 15 minutes with occasional shaking to adsorb the unreacted cAMP. After centrifuging, the radioactivity of the supernatant was measured by a liquid scintillation counter.

The action of the test compound on PDE activity was studied by calculating the inhibition percentage in the absence of calcium/calmodulin from the following formula, and represented as IC$_{50}$ value. The results were shown in Table 7.

$$\text{Inhibition precentage in the absence of calcium/calmodulin (\%)} = \left(1 - \frac{a}{b}\right) \times 100$$

a: PDE activity in the presence of test compound and in the absence of calmodulin b: PDE activity in the absence of test compound and calmoduline

TABLE 7

| Test compound (Example No.) | Inhibitory action on calcium/calmodulin dependent phosphodiesterase IC$_{50}$ (μM) |
| --- | --- |
| 57 | 11 |
| 62 | 11 |
| 65 | 20 |
| 67 | 7 |
| vinpocetine | 88 |

In the table, vinpocetine is a general name of (4-ethoxycarbonyl-(3α,16α-ethyl)-14,15-eburnamenine.

Experiment 8: Acute toxicity test

The acute toxicity of the compounds of the present invention was studied in 6 male mice. All mice survived at the dose of 1000 mg/kg of the compounds, for 5 days observation after the oral administration of the compound.

The compounds of the present invention and pharmaceutically acceptable acid addition salts thereof can be safely administered orally or parenterally in human beings in the form of a pharmaceutical composition such as tablets, pills, powder, capsules, granules, solutions, inhalants, suppositories, percutaneous absorption preparations or injectable solutions. The pharmaceutical composition can be prepared by, for example, mixing a therapeutically effective amount of at least one compound as an active ingredient with a pharmaceutically acceptable additives such as an excipient, an extender, a diluent or a solubilizer. The dose may vary depending upon the compound selected or employed, the severity of the patients to be treated or the age of the patients, but the daily dose for human adults preferably ranges from 0.1 to 500 mg in single or multiple dose.

The present invention will be explained by the following examples in detail, but these examples are not to be construed as limiting the present invention.

The compounds encompassed in formula (II) can be prepared by the following methods.

EXAMPLE 1

To a suspension of 143.6 g of 2-chlorocyanoacetophenone and 26.8 g of sulfur in 200 ml of dimethylformamide is added 84.9 g of triethylamine with stirring under ice-cooling. To the mixture is added 108 g of octylaldehyde in 60 ml of ethanol and stirred at 55°-60° C. for 3 hours. The resultant solution is poured into ice-cold water, extracted with 400 ml of toluene. The extract is washed with water and dried over anhydrous magnesium sulfate. After separating by filtration, the filtrate is concentrated under reduced pressure to give 200 g of 2-amino-3-(2-chlorobenzoyl)-5-hexylthiophene as oil.

To the solution of 200 g of thus obtained compound in 200 ml of chloroform is added 91 g of chloroacetyl chloride and the mixture is refluxed under heating with stirring for 2 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure and the residue is crystallized from isopropyl ether to give 105 g of 2-chloroacetamido-3-(2-chlorobenzoyl)-5-hexylthiophene as crystals.

The suspension of 25 g of the above-mentioned chloroacetamido compound and 10.4 g of sodium iodide in 100 ml of tetrahydrofuran is refluxed under heating with stirring for 2 hours. The reaction solution is cooled to −20° C. and about 10 ml of liquid ammonia is added thereto at once with stirring. The temperature of the resulting solution is gradually raised to room temperature over 2 hours. After the ammonia is removed with an aspirator, the mixture is concentrated under reduced pressure and the residue is dissolved in 200 ml of chloroform. The solution is washed with water and dried over anhydrous magnesium sulfate. After separating by filtration, the filtrate is concentrated under reduced pressure to give 27 g of 2-aminoacetamido-3-(2-chlorobenzoyl)-5-hexylthiophene as crude oil.

Then, to a solution of 27 g of the above-mentioned compound in 100 ml of isopropyl alcohol is added 5.6 g of acetic acid and the mixture is refluxed under heating with stirring for 5 hours. The mixture is concentrated under reduced pressure, the residue is dissolved in 200 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is crystallized from 50 ml of isopropyl ether to give 6.4 g of 5-(2-chlorophenyl)-7-hexyl-1,3-dihydro-thieno[2,3-e]-1,4-diazepin-2-one as crystals, melting at 141–143° C.

EXAMPLE 2

To a suspension of 35 g of 2-methoxycyanoacetophenone and 6.7 g of sulfur in 50 ml of dimethylformamide is added 21.2 g of triethylamine with stirring under ice-cooling. To the mixture is added 26.9 g of octylaldehyde in 15 ml of ethanol and stirred at 55–60° C. for 3 hours. The resultant solution is poured into ice-cold water, extracted with 300 ml of toluene. The extract is washed with water and dried over anhydrous magnesium sulfate. After separating by filtration, the filtrate is concentrated under reduced pressure to give 70 g of 2-amino-5-hexyl-3-(2-methoxybenzoyl)thiophene as oil.

To the solution of 70 g of thus obtained compound in 500 ml of chloroform is added 23 g of chloroacetyl chloride and the mixture is refluxed under heating with stirring for 2 hours. After cooling, the mixture is washed with 5% aqueous sodium hydrogencarbonate solution and sodium chloride solution, and dried over anhydrous magnesium sulfate; After separating by filtration, the filtrate is concentrated under reduced pressure and the residue is crystallized from hexane to give 37.8 g of 2-chloroacetamido-5-hexyl-3-(2-methoxybenzoyl)thiophene as crystals.

The suspension of 37.8 g of the above-mentioned chloroacetamido compound and 15.8 g of sodium iodide in 200 ml of tetrahydrofuran is refluxed under heating with stirring for 2 hours. The reaction solution is cooled to −20° C. and about 30 ml of liquid ammonia is added thereto at once. The temperature of the resulting solution is gradually raised to room temperature over 2 hours. After the ammonia is removed with an aspirator, the mixture is concentrated under reduced pressure and the residue is dissolved in 200 ml of chloroform. The solution is washed with water and dried over anhydrous magnesium sulfate. After separating by filtration, the filtrate is concentrated under reduced pressure to give 35 g of 2-aminoacetamido-3-(2-methoxybenzoyl)-5-hexylthiophene as crude oil.

Then, to a solution of 35 g of the above-mentioned compound in 150 ml of isopropyl alcohol is added 8.6 g of acetic acid and the mixture is refluxed under heating with stirring for 5 hours. The mixture is concentrated under reduced pressure, the residue is dissolved in 200 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is crystallized from ethyl acetate to give 12 g of 7-hexyl-5-(2-methoxyphenyl)-1,3-dihydro-2H-thieno[2,3-e]-1,4-diazepin-2-one as crystals, melting at 130°-132° C.

EXAMPLE 3

To a solution of 28 g of 2-amino-3-(4-methoxybenzoyl)-5-hexylthiophene in 150 ml of chloroform is added 10 g of chloroacetyl chloride and the mixture is refluxed under heating with stirring for 2 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure and the residue is crystallized from ethanol to give 16.2 g of 2-chloroacetamido-3-(4-methoxybenzoyl)-5-hexylthiophene as crystals.

The suspension of 16.2 g of the above-mentioned chloroacetamido compound and 6.8 g of sodium iodide in 100 ml of tetrahydrofuran is refluxed under heating with stirring for 2 hours. The reaction solution is cooled to −20° C. and about 20 ml of liquid ammonia is added thereto at once with stirring. The temperature of the resulting solution is gradually raised to room temperature over 2 hours. After the ammonia is removed with an aspirator, the mixture is concentrated under reduced pressure and the residue is dissolved in 150 ml of chloroform. The solution is washed with water and dried over anhydrous magnesium sulfate. After separating by filtration, the filtrate is concentrated under reduced pressure to give 20 g of 2-aminoacetamido-3-(4-methoxybenzoyl)-5-hexylthiophene as crude oil.

Then, to a solution of 20 g of the above-mentioned compound in 100 ml of isopropyl alcohol is added 4 g of acetic acid and the mixture is refluxed under heating with stirring for 5 hours. The mixture is concentrated under reduced pressure, the residue is dissolved in 100 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is crystallized from isopropyl ether to give 9 g of 7-hexyl-5-(4-methoxyphenyl)-1,3-dihydro-2H-thieno[2,3-e]-1,4-diazepin-2-one as crystals, melting at 123°–125° C.

EXAMPLE 4

To a suspension of 35.9 g of 2-chlorocyanoacetophenone and 6.7 g of sulfur in 50 ml of dimethylformamide is added 21.2 g of triethylamine with stirring under ice-cooling. To the mixture is added 38.7 g of dodecylaldehyde in 15 ml of ethanol and stirred at 55–60° C. for 3 hours. The resultant solution is poured into ice-cold water, extracted with 400 ml of toluene. The extract is washed with water and dried over anhydrous magnesium sulfate. After separating by filtration, the filtrate is concentrated under reduced pressure to give 75 g of 2-amino-3-(2-chlorobenzoyl)-5-decylthiophene as crude oil.

To the solution of 75 g of thus obtained compound in 600 ml of chloroform is added 63 g of chloroacetyl chloride and the mixture is refluxed under heating with stirring for 2 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure and the residue is crystallized from hexane to give 32 g of 2-chloroacetamido-3-(2-chlorobenzoyl)-5-decylthiophene as crystals.

The suspension of 32 g of the above-mentioned chloroacetamido compound and 11.6 g of sodium iodide in 150 ml of tetrahydrofuran is refluxed under heating with stirring for 2.5 hours. The reaction solution is cooled to −20° C. and about 30 ml of liquid ammonia is added thereto at once with stirring. The temperature of the resulting solution is gradually raised to room temperature over 2 hours. After the ammonia is removed with an aspirator, the mixture is concentrated under reduced pressure and the residue is dissolved in 150 ml of chloroform. The solution is washed with water and dried over anhydrous magnesium sulfate. After separating by filtration, the filtrate is concentrated under reduced pressure to give 35 g of 2-aminoacetamido-3-(2-chlorobenzoyl)-5-decylthiophene as crude oil.

Then, to a solution of 35 g of the above-mentioned compound in 100 ml of isopropyl alcohol is added 5.6 g of acetic acid and the mixture is refluxed under heating with stirring for 5 hours. The mixture is concentrated under reduced pressure, the residue is dissolved in 200 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is subjected to chromatography on silica gel to give 23 g of 5-(2-chlorophenyl)-7 decyl-1,3-dihydro-2H-thieno[2,3-e]-1,4-diazepin-2-one as oil.

EXAMPLE 5

To a suspension of 35 g of 2-methoxycyanoacetophenone and 6.7 g of sulfur in 50 ml of dimethylformamide is added 21.2 g of triethylamine with stirring under ice-cooling. To the mixture is added 33 g of decylaldehyde in 15 ml of ethanol and stirred at 55°–60° C. for 3 hours. The resultant solution is poured into ice-cold water, extracted with 400 ml of toluene. The extract is washed with water and dried over anhydrous magnesium sulfate. After separating by filtration, the filtrate is concentrated under reduced pressure to give 80 g of 2-amino-3-(2-methoxybenzoyl)-5-octylthiophene as oil.

To the solution of 80 g of thus obtained compound in 500 ml of chloroform is added 23 g of chloroacetyl chloride and the mixture is refluxed under heating with stirring for 2.5 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure and the residue is crystallized from hexane to give 62 g of 2-chloroacetamido-3-(2-methoxybenzoyl)-5-octylthiophene as crystals.

The suspension of 42 g of the above-mentioned chloroacetamido compound and 16.5 g of sodium iodide in 200 ml of tetrahydrofuran is refluxed under heating with stirring for 2 hours. The reaction solution is cooled to −20° C. and about 30 ml of liquid ammonia is added thereto at once with stirring. The temperature of the resulting solution is gradually raised to room temperature over 2 hours. After the ammonia is removed with an aspirator, the mixture is concentrated under reduced pressure and the residue is dissolved in 200 ml of chloroform. The solution is washed with water and dried over anhydrous magnesium sulfate. After separating by filtration, the filtrate is concentrated under reduced pressure to give 45 g of 2-aminoacetamido-3-(2-methoxybenzoyl)-5-octylthiophene as crude oil.

Then, to a solution of 45 g of the above-mentioned compound in 200 ml of isopropyl alcohol is added 9 g of acetic acid and the mixture is refluxed under heating with stirring for 5 hours. The mixture is concentrated under reduced pressure, the residue is dissolved in 200 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is crystallized from isopropyl ether-ethyl acetate to give 14 g of 5-(2-methoxyphenyl)-7-octyl-1,3-dihydro-2H-thieno[2,3-e]-1,4-diazepin-2-one as crystals, melting at 128°–130° C.

EXAMPLE 6

To a suspension of 71.8 g of 2-chlorocyanoacetophenone and 13.4 g of sulfur in 100 ml of dimethylformamide is added 42.5 g of triethylamine with stirring under ice-cooling. To the mixture is added 65.6 g of decylaldehyde in 30 ml of ethanol and stirred at 55–60° C. for 3 hours. The resultant solution is poured into ice-cold water, extracted with 400 ml of toluene. The extract is washed with water and dried over anhydrous magnesium sulfate. After separating by filtration, the filtrate is concentrated under reduced pressure to give 120 g of 2-amino-3-(2-chlorobenzoyl)-5-octylthiophene as crude oil.

To the solution of 120 g of thus obtained compound in 500 ml of chloroform is added 45 g of chloroacetyl chloride and the mixture is refluxed under heating with stirring for 2 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure to give 150 g of 2-chloroacetamido-3-(2-chlorobenzoyl)-5-octylthiophene as crude oil.

The suspension of 150 g of the above-mentioned chloroacetamido compound and 60 g of sodium iodide in 300 ml of tetrahydrofuran is refluxed under heating with stirring for 4 hours. The reaction solution is cooled to −20° C. and about 50 ml of liquid ammonia is added thereto at once with stirring. The temperature of the resulting solution is gradually raised to room temperature over 2 hours. After the ammonia is removed, the mixture is concentrated under reduced pressure and the residue is dissolved in 400 ml of chloroform. The solution is washed with water and dried over anhydrous magnesium sulfate. After separating by filtration, the filtrate is concentrated under reduced pressure to give 155 g of 2-aminoacetamido-3-(2-chlorobenzoyl)-5-octylthiophene as crude oil.

Then, to a solution of 155 g of the aminoacetamido compound in 300 ml of isopropyl alcohol is added 30 g of acetic acid and the mixture is refluxed under heating with stirring for 5 hours. The mixture is concentrated under reduced pressure, the residue is dissolved in 300 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is subjected to chromatography on silica gel to give 30 g of 5-(2-chlorophenyl)-7-octyl-1,3-dihydro-2H-thieno[2,3-e]-1,4-diazepin-2-one as crystals, melting at 131°–133° C.

Example 7

To a suspension of 31.8 g of 2-methylcyanoacetophenone and 6.7 g of sulfur in 50 ml of dimethylformamide is added 21.2 g of triethylamine with stirring under ice-cooling. To the mixture is added 33 g of decylaldehyde in 15 ml of ethanol and stirred at 55°–60° C. for 5 hours. The resultant solution is poured into ice-cold water, extracted with 400 ml of toluene. The extract is washed with water and dried over anhydrous magnesium sulfate. After separating by filtration, the filtrate is concentrated under reduced pressure to give 70 g of 2-amino-3-(2-methylbenzoyl)-5 decylthiophene as crude oil.

To the solution of 70 g of thus obtained compound in 300 ml of chloroform is added 23 g of chloroacetyl chloride and the mixture is refluxed under heating with stirring for 2 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure to give 85 g of 2-chloroacetamido-3-(2-methylbenzoyl)-5-decylthiophene as crude oil.

The suspension of 85 g of the above-mentioned chloroacetamido compound and 33 g of sodium iodide in 200 ml of tetrahydrofuran is refluxed under heating with stirring for 2.5 hours. The reaction solution is cooled to −20° C. and about 30 ml of liquid ammonia is added thereto at once with stirring. The temperature of the resulting solution is gradually raised to room temperature over 2 hours. After the ammonia is removed, the mixture is concentrated under reduced pressure and the residue is dissolved in 200 ml of chloroform. The solution is washed with water and dried over anhydrous magnesium sulfate. After separating by filtration, the filtrate is concentrated under reduced pressure to give 2-aminoacetamido-3-(2-methylbenzoyl)-5-decylthiophene as crude oil.

Then, to a solution of the 2-aminoacetamido compound in 300 ml of isopropyl alcohol is added 18 g of acetic acid and the mixture is refluxed under heating with stirring for 5 hours. The mixture is concentrated under reduced pressure, the residue is dissolved in 300 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is subjected to chromatography on silica gel to give 14.9 g of 7-decyl-5-(2-methylphenyl)-1,3-dihydro-2H-thieno[2,3-e]-1,4-diazepin-2-one as crystals, melting at 100°–102° C.

EXAMPLE 8

To a suspension of 31.8 g of 2-methylcyanoacetophenone and 6.7 g of sulfur in 50 ml of dimethylformamide is added 21 g of triethylamine with stirring under ice-cooling. To the mixture is added 27 g of octylaldehyde in 15 ml of ethanol and stirred at 55-60° C. for 3 hours. The resultant solution is poured into ice-cold water, extracted with 500 ml of toluene. The extract is washed with water and dried over anhydrous magnesium sulfate. After separating by filtration, the filtrate is concentrated under reduced pressure to give 50 g of 2-amino-3-(2-methylbenzoyl)-5-hexylthiophene as crude oil.

To the solution of 50 g of thus obtained compound in 500 ml of chloroform is added 25 g of chloroacetyl chloride and the mixture is refluxed under heating with stirring for an hour. After cooling, the mixture is washed with 5% aqueous sodium hydrogencarbonate solution and sodium chloride solution, and dried over anhydrous magnesium sulfate. After separating by filtration, the filtrate is concentrated under reduced pressure and the residue is crystallized from hexane to give 28 g of 2-chloroacetamido-3-(2-methylbenzoyl)-5-hexylthiophene as crystals.

The suspension of 28 g of the above-mentioned chloroacetamido compound and 12 g of sodium iodide in 200 ml of tetrahydrofuran is refluxed under heating with stirring for 4 hours. The reaction solution is cooled to −20° C. and about 30 ml of liquid ammonia is added thereto at once with stirring. The temperature of the resulting solution is gradually raised to room temperature over 2 hours. After the ammonia is removed, the mixture is concentrated under reduced pressure and the residue is dissolved in 200 ml of chloroform. The solution is washed with water and dried over anhydrous magnesium sulfate. After separating by filtration, the filtrate is concentrated under reduced pressure to give 25 g of 2-aminoacetamido-3-(2-methylbenzoyl)-5-hexylthiophene as crude oil.

Then, to a solution of 25 g of the above-mentioned compound in the mixture of 100 ml of pyridine and 50 ml of toluene is added 4.5 g of acetic acid and the mixture is refluxed under heating with stirring for overnight. The mixture is concentrated under reduced pressure, the residue is dissolved in 200 ml of chloroform, washed with 5% hydrochloric acid solution and sodium chloride solution, and then dried over anhydrous magnesium sulfate. After separating by filtration, the filtrate is concentrated under reduced pressure and the residue is subjected to chromatography on silica gel to give 5 g of 7-hexyl-5-(2-methylphenyl)-1,3-dihydro-2H-thieno[2,3-e]-1,4-diazepin-2-one as crystals, melting at 162°–163° C.

EXAMPLE 9

To a suspension of 35.9 g of 2-chlorocyanoacetophenone and 6.7 g of sulfur in 50 ml of dimethylformamide is added 21 g of triethylamine with stirring under ice-cooling. To the mixture is added 53 g of tetradecylaldehyde in 15 ml of ethanol and stirred at 55°–60° C. for 3 hours. The resultant solution is poured into ice-cold water, extracted with 400 ml of ethyl acetate. The extract is washed with water and dried over anhydrous magnesium sulfate. After separating by filtration, the filtrate is concentrated under reduced pressure to give 75 g of 2-amino-3-(2-chlorobenzoyl)-5-dodecylthiophene as crude oil.

To the solution of 75 g of thus obtained compound in 500 ml of chloroform is added 22 g of chloroacetyl chloride and the mixture is refluxed under heating with stirring for 2 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure and the residue is crystallized from hexane to give 57.5 g of 2-chloroacetamido-3-(2-chlorobenzoyl)-5-dodecylthiophene as crystals.

The suspension of 57.5 g of the above-mentioned 2-chloroacetamido compound and 19 g of sodium iodide in 200 ml of tetrahydrofuran is refluxed under heating with stirring for 2.5 hours. The reaction solution is cooled to −20° C. and about 50 ml of liquid ammonia is added thereto at once with stirring. The temperature of the resulting solution is gradually raised to room temperature over 2 hours. After the ammonia is removed, the mixture is concentrated under reduced pressure and the residue is dissolved in 200 ml of chloroform. The solution is washed with water and dried over anhydrous magnesium sulfate. After separating by filtration, the filtrate is concentrated under reduced pressure to give 60 g of 2-aminoacetamido-3-(2-chlorobenzoyl)-5-dodecylthiophene.

Then, to a solution of 60 g of the aminoacetamido compound in 300 ml of isopropyl alcohol is added 11 g of acetic acid and the mixture is refluxed under heating with stirring for 4 hours. The mixture is concentrated under reduced pressure, the residue is dissolved in 300 ml of chloroform, washed with 5% aqueous sodium hydrogencarbonate solution and sodium chloride solution, and then dried over anhydrous magnesium sulfate. After separating by filtration, the filtrate is crystallized from hexane to give 6.4 g of 5-(2-chlorophenyl)-7-dodecyl-1,3-dihydro-2H-thieno[2,3-e]-1,4-diazepin-2-one as crystals, melting at 119°–121° C.

EXAMPLE 10

To a suspension of 26 g of 2-chlorocyanoacetophenone and 4.7 g of sulfur in 50 ml of dimethylformamide is added 13.6 g of triethylamine with stirring under ice-cooling. To the mixture is added 36 g of octadecylaldehyde in 15 ml of ethanol and stirred at 50-60° C. for 10 hours. The resultant solution is poured into ice-cold water, extracted with 400 ml of ethyl acetate. The extract is washed with water and dried over anhydrous magnesium sulfate. After separating by filtration, the filtrate is concentrated under reduced pressure to give 57 g of 2-amino-3-(2-chlorobenzoyl)-5-hexadecylthiophene as crude oil.

To the solution of 57 g of thus obtained compound in 400 ml of chloroform is added 15 g of chloroacetyl chloride and the mixture is refluxed under heating with stirring for 1.5 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure to give about 60 g of 2-chloroacetamido-3-(2-chlorobenzoyl)-5-hexadecylthiophene as crude oil.

The suspension of 60 g of the above-mentioned chloroacetamido compound and 20 g of sodium iodide in 200 ml of tetrahydrofuran is refluxed under heating with stirring for 2 hours. The reaction solution is cooled to −20° C. and about 40 ml of liquid ammonia is added thereto at once with stirring. The temperature of the resulting solution is gradually raised to room temperature over 2 hours. After the ammonia is removed, the mixture is concentrated under reduced pressure and the residue is dissolved in 200 ml of chloroform. The solution is washed with water and dried over anhydrous magnesium sulfate. After separating by filtration, the filtrate is concentrated under reduced pressure and the residue is dissolved in 300 ml of isopropyl alcohol. To the solution is added 12 g of acetic acid and the mixture is refluxed under heating with stirring overnight. The mixture is concentrated under reduced pressure, the residue is dissolved in 300 ml of chloroform, washed with 5% aqueous sodium hydrogencarbonate solution and sodium chloride solution, and then dried over anhydrous magnesium sulfate. After separating by filtration, the filtrate is concentrated under reduced pressure and the residue is subjected to chromatography on silica gel to give 7 g of 5-(2-chlorophenyl)-7-hexadecyl-1,3-dihydro-2H-thieno[2,3-e]-1,4-diazepin-2-one as oil.

EXAMPLE 11

To a solution of 62 g of 2-amino-5-hexyl-3-(2-methylbenzoyl)-thiophene, which is obtained in Example 8, in 200 ml of chloroform is added 47.3 g of (DL)-N-phthalylalanyl chloride and the mixture is refluxed under heating with stirring for 2 hours. After cooling, the mixture is washed with water and 5% aqueous sodium hydrogencarbonate solution, and dried over anhydrous magnesium sulfate. After separating by filtration, the filtrate is concentrated under reduced pressure and the residue is crystallized from ethanol to give 65 g of 5-hexyl-3-(2-methylbenzoyl)-2-(N-phthalylalanyl)amino-thiophene as crystals, melting at 95°–97° C.

To a suspension of 30.2 g of the thus obtained compound in 300 ml of methanol is added 8.3 g of methylhydrazine under ice-cooling and the mixture is stirred at room temperature for 30 minutes. To the mixture is added 20 ml of concentrated hydrochloric acid and the mixture is further refluxed under heating for 2 hours. After the mixture is concentrated under reduced pressure, to the residue is added 150 ml of chloroform and the resulting pyridazinone is filtered off. The chloroform layer is washed with 5% aqueous sodium hydrogencarbonate solution and dried over anhydrous magnesium sulfate. After separating by filtration, the filtrate is concentrated under reduced pressure and the resulting crude oil of 2-(N-alanyl)amino-5-hexyl-3-(2-methylbenzoyl)-thiophene is dissolved in 200 ml of isopropyl alcohol. To the solution is added 4.3 g of acetic acid and the mixture is refluxed under heating with stirring for 14 hours. After cooling, the mixture is concentrated under reduced pressure and the residue is crystallized from isopropyl ether to give 11.6 g of 7-hexyl-3-methyl-5-(2-methylphenyl)-1,3-dihydro-2H-thieno[2,3-e]-1,4-diazepin-2-one as colorless crystals, melting at 173°–175° C.

The following compounds can be prepared in a similar manner.

(12) 7-hexyl-5-(4-methylphenyl)-1,3-dihydro-2H-thieno[2,3-e]-1,4-diazepin-2-one, melting at 138°–140° C.

(13) 7-hexyl-5-(3-methylphenyl)-1,3-dihydro-2H-thieno[2,3-e]-1,4-diazepin-2-one, melting at 103°–105° C.

(14) 7-hexyl-5-(2,4-dimethylphenyl)-1,3-dihydro-2H-thieno[2,3-e]-1,4-diazepin-2-one, melting at 147°–150° C.

(15) 7-hexyl-5-(2,3-dimethylphenyl)-1,3-dihydro-2H-thieno[2,3-e]-1,4-diazepin-2-one, melting at 161°–163° C.

(16) 7-hexyl-5-(3,4-dimethylphenyl)-1,3-dihydro-2H-thieno[2,3-e]-1,4-diazepin-2-one, melting at 120°–122° C.

(17) 7-hexyl-5-(3,4,5-trimethoxyphenyl)-1,3-dihydro-2H-thieno[2,3-e]-1,4-diazepin-2-one, melting at 127°–129° C.

(18) 7-hexyl-5-(2,5-dimethylphenyl)-1,3-dihydro-2H-thieno[2,3-e]-1,4-diazepin-2-one, melting at 123°–125° C.

(19) 7-decyl-5-(2-methoxyphenyl)-1,3-dihydro-2H-thieno[2,3-e]1,4-diazepin-2-one, melting at 132°–133° C.

(20) 5-(2-chlorophenyl)-7-(1,5-dimethyl-4-hexenyl)-1,3-dihydro2H-thieno[2,3-e]-1,4-diazepin-2-one, melting at 123°–125° C.

(21) 7-hexyl-3-methyl-5-(2-methoxyphenyl)-1,3-dihydro-2H-thieno[2,3-e]-1,4-diazepin-2-one, melting at 187°–189° C.

(22) 5-(2-chlorophenyl)-7-hexyl-3-methyl-1,3-dihydro-2H-thieno[2,3-e]-1,4-diazepin-2 one, melting at 169°–171° C.

(23) 5-(2-methylphenyl)-7-octyl-1,3-dihydro-2H-thieno[2,3-e]-1,4-diazepin-2-one

(24) 5-(3-methylphenyl)-7-octyl-1,3-dihydro-2H-thieno[2,3-e]-1,4-diazepin-2-one

(25) 5-(4-methylphenyl)-7-octyl-1,3-dihydro-2H-thieno[2,3-e]-1,4-diazepin-2-one

(26) 5-(2,3-dimethylphenyl)-7-octyl-1,3-dihydro-2H-thieno[2,3-e]-1,4-diazepin-2-one

(27) 5-(2,4-dimethylphenyl)-7-octyl-1,3-dihydro-2H-thieno[2,3-e]-1,4-diazepin-2-one

(28) 5-(3,4-dimethylphenyl)-7-octyl-1,3-dihydro-2H-thieno[2,3-e]-1,4-diazepin-2-one

(29) 5-(3,4,5-trimethoxyphenyl)-7-octyl-1,3-dihydro-2H-thieno[2,3-e]-1,4-diazepin-2-one

(30) 7-decyl-5-(3,4,5-trimethoxyphenyl)-1,3-dihydro-2H-thieno[2,3-e]-1,4-diazepin-2-one

(31) 7-hexyl-5-(2,3-dimethoxyphenyl)-1,3-dihydro-2H-thieno[2,3-e]-1,4-diazepin-2-one

(32) 7-hexyl-5-(2,6-dimethoxyphenyl)-1,3-dihydro-2H-thieno[2,3-e]-1,4-diazepin-2-one

(33) 5-(2,6-dimethoxyphenyl)-7-octyl-1,3-dihydro-2H-thieno[2,3-e]-1,4-diazepin-2-one

(34) 7-decyl-5-(2,6-dimethoxyphenyl)-1,3-dihydro-2H-thieno[2,3-e]-1,4-diazepin-2-one

(35) 5-(2,3-dimethoxyphenyl)-7-octyl-1,3-dihydro-2H-thieno[2,3-e]-1,4-diazepin-2-one

(36) 7-decyl-5-(2,3-dimethoxyphenyl)-1,3-dihydro-2H-thieno[2,3-e]-1,4-diazepin-2-one

(37) 7-hexyl-5-(3,4-dimethoxyphenyl)-1,3-dihydro-2H-thieno[2,3-e]-1,4-diazepin-2-one

(38) 5-(3,4-dimethoxyphenyl)-7-octyl-1,3-dihydro-2H-thieno[2,3-e]-1,4-diazepin-2-one

(39) 7-hexyl-5-(3,5-dimethoxyphenyl)-1,3-dihydro-2H-thieno[2,3-e]-1,4-diazepin-2-one

(40) 5-(3-chlorophenyl)-7-hexyl-1,3-dihydro-2H-thieno[2,3-e]-1,4-diazepin-2-one

(41) 5-(4-chlorophenyl)-7-hexyl-1,3-dihydro-2H-thieno[2,3-e]-1,4-diazepin-2-one

(42) 5-(3,4-dichlorophenyl)-7-hexyl-1,3-dihydro-2H-thieno[2,3-e]-1,4-diazepin-2-one

(43) 5-(3,4-dichlorophenyl)-7-octyl-1,3-dihydro-2H-thieno[2,3-e]-1,4-diazepin-2-one

(44) 5-(3,4-dichlorophenyl)-7-decyl-1,3-dihydro-2H-thieno[2,3-e]-1,4-diazepin-2-one

(45) 5-(2,4-dichlorophenyl)-7-hexyl-1,3-dihydro-2H-thieno[2,3-e]-1,4-diazepin-2-one

(46) 5-(2,5-dichlorophenyl)-7-hexyl-1,3-dihydro-2H-thieno[2,3-e]-1,4-diazepin-2-one

(47) 5-(2-bromophenyl)-7-hexyl-1,3-dihydro-2H-thieno[2,3-e]-1,4-diazepin-2-one

(48) 5-(2-bromophenyl)-7-octyl-1,3-dihydro-2H-thieno[2,3-e]-1,4-diazepin-2-one

(49) 7-hexyl-3,6-dimethyl-5-(2-methylphenyl)-1,3-dihydro-2H-thieno[2,3-e]-1,4-diazepin-2-one

(50) 3-ethyl-7-hexyl-5-(2-methylphenyl)-1,3-dihydro-2H-thieno[2,3-e]-1,4-diazepin-2-one

(51) 7-hexyl-5-(2-methylphenyl)-3-propyl-1,3-dihydro-2H-thieno-[2,3-e]-1,4-diazepin-2-one

(52) 7-hexyl-5-(3,4,5-trimethoxyphenyl)-3-methyl-1,3-dihydro2H-thieno[2,3-e]-1,4-diazepin-2-one

(53) 7-hexyl-5-(3,4-methylenedioxyphenyl)-1,3-dihydro-2H-thieno[2,3-e]-1,4-diazepin-2-one The following compounds which are embraced in formula (I) can be prepared by using the compounds obtained in the above examples.

EXAMPLE 54

A suspension of 25.6 g of 5-(2-chlorophenyl)-7-hexyl-1,3-dihydro-2H-thieno[2,3-e]-1,4-diazepin-2-one and 7.2 g of phosphorus pentasulfide in 140 ml of pyridine is stirred at 80°–90° C. for 2 hours. The resultant solution is poured into 300 ml of ice-cold water with stirring and the precipitated crystals are collected by filtration. The crystals are recrystallized from isopropyl alcohol to give 21.1 g of thione compound, melting at 154°–156° C. To a suspension of 4.5 g of the thione compound in 50 ml of methanol is added 2 g of 100% hydrazine monohydrate under ice-cooling and stirred for 30 minutes. The mixture is concentrated under reduced pressure at 30°–40° C. and subjected to azeotropic distillation with toluene three times. To the solution of the residue in 50 ml of toluene are added 1.5 g of acetic anhydride and 4.3 g of acetic acid and refluxed under heating for 7 hours. The mixture is concentrated under reduced pressure and the residue is dissolved in 50 ml of chloroform. The solution is washed with 5% aqueous sodium hydrogencarbonate solution and water, and dried over anhydrous magnesium sulfate. After concentrating under reduced pressure, the oily residue is subjected to chromatography on silica gel and eluted with a mixture of chloroform-methanol (100 : 1 to 100 : 3). The eluate of the objective fraction is concentrated under reduced pressure and the residue is crystallized from isopropyl ether to give 1.2 g of 4-(2-chlorophenyl)-2-hexyl-9-methyl-6H-thieno[3,2-f][1,2,4]triazolo[4,3-a][1,4]diazepine as crystals, melting at 111°–113° C.

The above compound can also be prepared by reacting the thione compound with acethydrazide

EXAMPLE 55

A mixture of 12 g of 7-hexyl-5-(2-methoxyphenyl)-1,3-dihydro-2H-thieno[2,3-e]-1,4-diazepin-2-one and 3.4 g of phosphorus pentasulfide in 80 ml of pyridine is stirred at 75°–80° C. for 3 hours. The resultant solution is poured into 200 ml of ice-cold water with stirring and stirred for about 1.5 hours. The precipitated crystals are collected by filtration, washed with water and then dried to give 12.6 g of thione compound. To a suspension of 12.6 g of the thione compound in 150 ml of methanol is added 5.5 g of 100% hydrazine monohydrate under ice-cooling with stirring and stirred for an hour. The mixture is concentrated under reduced pressure at 30°-35° C. and the residue is dissolved in 200 ml of chloroform. The solution is washed with sodium chloride solution and dried over anhydrous magnesium sulfate. After separating by filtration, the filtrate is concentrated and the residue is dissolved in 100 ml of toluene. To the solution are added 4.2 g of acetic anhydride and 12.2 g of acetic acid and the mixture is refluxed under heating for 2 hours. After the mixture is concentrated under reduced pressure, the residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the resulting oily residue is subjected to chromatography on silica gel and eluted with a mixture of chloroform-methanol (100:1 to 100:3). The eluate of the objective fraction is concentrated under reduced pressure and the residue is crystallized from ethyl acetate to give 3.3 g of 2-hexyl-4-(2-methoxyphenyl)-9-methyl-6H-thieno[3,2-f][1,2,4]triazolo[4,3-a][1,4]diazepine as crystals, melting at 128°-130° C.

EXAMPLE 56

A mixture of 9 g of 7-hexyl-5-(4-methoxyphenyl)-1,3-dihydro-2H-thieno[2,3-e]-1,4-diazepin-2-one and 2.6 g of phosphorus pentasulfide in 50 ml of pyridine is stirred at 80°-90° C. for 2 hours. The resultant solution is poured into 100 ml of ice-cold water with stirring. The precipitated crystals are collected by filtration, washed with water and then cried to give 10 g of thione compound To a suspension of 10 g of the thione compound in 75 ml of methanol is added 3.3 g of 100% hydrazine hydrate under ice-cooling with stirring and stirred for 45 minutes. The mixture is concentrated under reduced pressure at 30°-40° C. and the residue is dissolved in 100 ml of chloroform. The solution is washed with saturated sodium chloride solution and dried over anhydrous magnesium sulfate. After separating by filtration, the filtrate is concentrated and the residue is dissolved in 75 ml of toluene. To the solution are added 2.5 g of acetic anhydride and 7.2 g of acetic acid and the mixture is refluxed under heating for 5 hours. After the mixture is concentrated under reduced pressure, the residue is dissolved in 100 ml of chloroform, and the solution is washed with 5% aqueous sodium hydrogen-carbonate solution and sodium chloride solution and dried over anhydrous magnesium sulfate. After separating by filtration, the filtrate is concentrated under reduced pressure, and the resulting oily residue is subjected to chromatography on silica gel and eluted with a mixture of chloroform-methanol (100:1 to 100:3). The eluate of the objective fraction is concentrated under reduced pressure and the residue is crystallized from isopropyl ether to give 0.27 g of 2-hexyl-4-(4-methoxyphenyl)-9-methyl-6H-thieno[3,2-f][1,2,4]triazolo[4,3-a][1,4]diazepine as crystals, melting at 97°-99° C.

EXAMPLE 57

A mixture of 11.7 g of 5-(2-chlorophenyl)-7-octyl-1,3-dihydro-2H-thieno[2,3-e]-1,4-diazepin-2-one and 3 g of phosphorus pentasulfide in 80 ml of pyridine is stirred at 80°-90° C. for 2 hours. The resultant solution is poured into 160 ml of ice-cold water with stirring The precipitated crystals are collected by filtration, washed with water and then cried to give 11.7 g of thione compound To a suspension of 11.7 g of the thione compound in 120 ml of methanol is added 4.8 g of 100% hydrazine hydrate under ice-cooling with stirring and stirred for an hour. The mixture is concentrated under reduced pressure at 30°-40° C. and the residue is dissolved in 100 ml of chloroform. The solution is washed with ice-cold water and dried over anhydrous magnesium sulfate. After separating by filtration, the filtrate is concentrated and the residue is dissolved in 100 ml of toluene. To the solution are added 3.5 g of acetic anhydride and 10 g of acetic acid and the mixture is refluxed under heating for 2 hours. After the mixture is concentrated under reduced pressure, the residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the resulting oily residue is subjected to chromatography on silica gel and eluted with a mixture of chloroform-methanol (100:1 to 100:3). The eluate of the objective fraction is concentrated under reduced pressure and the residue is crystallized from isopropyl ether to give 3.1 g of 4-(2-chlorophenyl)-2-octyl-9-methyl-6H-thieno[3,2-f][1,2,4]triazolo[4,3-a][1,4]diazepine as crystals, melting at 80°-82° C.

EXAMPLE 58

A mixture of 4.7 g of 7-hexyl-5-(2-methylphenyl)-1,3-dihydro-2H-thieno[2,3-e]-1,4-diazepin-2-one and 1.4 g of phosphorus pentasulfide in 50 ml of pyridine is stirred at 80°-90° C. for 3 hours. The resultant solution is poured into ice-cold water with stirring The precipitated crystals are collected by filtration, washed with water and then dried to give 4.6 g of thione compound To a suspension of 4.6 g of the thione compound in 50 ml of methanol is added 2.1 g of 100% hydrazine hydrate under ice-cooling with stirring and stirred for an hour. The mixture is concentrated under reduced pressure at 30°-40° C. and the residue is dissolved in 100 ml of chloroform. The solution is dried over anhydrous magnesium sulfate. After separating by filtration, the filtrate is concentrated and the residue is dissolved in 100 ml of toluene. To the solution are added 1.6 g of acetic anhydride and 4.7 g of acetic acid and the mixture is refluxed under heating for 2 hours. After the mixture is concentrated under reduced pressure, the residue is dissolved in 100 ml of chloroform, and the solution is washed with 5% aqueous sodium hydrogencarbonate solution and sodium chloride solution and dried over anhydrous magnesium sulfate After separating by filtration, the filtrate is concentrated under reduced pressure, and the resulting oily residue is subjected to chromatography on silica gel and eluted with a mixture of chloroform-methanol (100:1 to 100:3). The eluate of the objective fraction is concentrated under reduced pressure and the residue is crystallized from isopropyl ether to give 2.9 g of 2-hexyl-4-(2-methylphenyl)-9-methyl-6H-thieno[3,2-f][1,2,4]triazolo[4,3-a][1,4]diazepine as crystals, melting at 135°-137° C.

EXAMPLE 59

A mixture of 14 g of 5-(2-methoxyphenyl)-7-octyl-1,3-dihydro-2H-thieno[2,3-e]-1,4-diazepine-2-one and 3.7 g of phosphorus pentasulfide in 80 ml of pyridine is stirred at 83 -85° C. for 3 hours. The resultant solution is poured into ice-cold water with stirring The precipitated crystals are collected by filtration, washed with water and then dried to give 14.7 g of thione compound To a suspension of 14.7 g of the thione compound in 150 ml of methanol is added 6 g of 100% hydrazine hydrate under ice-cooling with stirring and stirred for 30 minutes The mixture is concentrated under reduced pressure at 30°–40° C. and the residue is dissolved in 100 ml of chloroform The solution is dried over anhydrous magnesium sulfate After separating by filtration, the filtrate is concentrated and the residue is dissolved in 100 ml of toluene. To the solution are added 4.5 g of acetic anhydride and 6.7 g of acetic acid and the mixture is refluxed under heating for 3 hours. After the mixture is concentrated under reduced pressure, the residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the resulting oily residue is subjected to chromatography on silica gel and eluted with a mixture of chloroform-methanol (100:1 to 100:3). The eluate of the objective fraction is concentrated under reduced pressure to give 3 g of 4-(2-methoxyphenyl)-9-methyl-2-octyl-6H-thieno[3,2-f][1,2,4]triazolo[4,3-a][1,4]diazepine as oil.

EXAMPLE 60

A mixture of 6.6 g of 5-(2-chlorophenyl)-7-(1,5-dimethyl-4-hexenyl)-1,3-dihydro-2H-thieno[2,3-e]-1,4-diazepin-2-one and 1.9 g of phosphorus pentasulfide in 70 ml of pyridine is stirred at 85°–95° C. for 3 hours. The resultant solution is poured into 150 ml of ice-cold water with stirring. The precipitated crystals are collected by filtration, washed with water and then dried to give 7.5 g of thione compound as crystals, melting at 159°–160° C. To a suspension of 7.5 g of the thione compound in 100 ml of methanol is added 3 g of 100% hydrazine hydrate under ice-cooling with stirring and stirred for 30 minutes. The mixture is concentrated under reduced pressure at 30°–40° C. and the residue is dissolved in 100 ml of chloroform. The solution is washed with ice-cold water and dried over anhydrous magnesium sulfate After separating by filtration, the filtrate is concentrated and the residue is dissolved in 100 ml of toluene To the solution are added 1 g of acetic anhydride and 2.7 g of acetic acid and the mixture is refluxed under heating for an hour. After the mixture is concentrated under reduced pressure, the residue is dissolved in 100 ml of chloroform, and the solution is washed with 5% aqueous sodium hydrogencarbonate solution and sodium chloride solution and dried over anhydrous magnesium sulfate After separating by filtration, the filtrate is concentrated under reduced pressure, and the resulting oily residue is subjected to chromatography on silica gel and eluted with a mixture of chloroform-methanol (100:1 to 100:3). The eluate of the objective fraction is concentrated under reduced pressure and the residue is crystallized from isopropyl ether to give 1.5 g of 4-(2-chlorophenyl)-2-(1,5-dimethyl-4-hexenyl-9 methyl-6H-thieno[3,2-f][1,2,4]triazolo[4,3-a][1,4]diazepine as crystals, melting at 122°–126° C.

EXAMPLE 61

A mixture of 5.1 g of 7-hexyl-5-(4-methylphenyl)-1,3-dihydro-2H-thieno[2,3-e]-1,4-diazepin-2-one and 3.7 g of Lawesson reagent in 100 ml of toluene is stirred at 30°–40° C. for an hour. The resultant solution is concentrated under reduced pressure, and the residue is subjected to chromatography on silica gel and then eluted with a mixture of chloroform-methanol (100:1 to 100:3). The eluate of the objective fraction is concentrated under reduced pressure to give 5.2 g of thione compound as crystals.

To a suspension of 5.2 g of thus obtained thione compound in 50 ml of methanol is added 2.4 g of 100% hydrazine monohydrate under ice-cooling with stirring and the mixture is stirred for an hour. After the mixture is concentrated under reduced pressure at 30° C, the residue is dissolved in 100 ml of chloroform and the solution is dried over anhydrous magnesium sulfate. After separating by filtration, the filtrate is concentrated under reduced pressure and the residue is dissolved in 100 ml of toluene. To the solution are added 3.6 g of acetic anhydride and 5.2 g of acetic acid, and the mixture is refluxed under heating for 2 hours and then concentrated under reduced pressure. The residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the residue is subjected to chromatography on silica gel and then eluted with a mixture of ethyl acetate-methanol (100:1 to 100:10). The eluate of the objective fraction is concentrated under reduced pressure and the residue is crystallized from a mixture of isopropyl ether-ethyl acetate to give 3.2 g of 2-hexyl-4-(4-methylphenyl)- 9-methyl-6H-thieno[3,2-f][1,2,4]triazolo[4,3-a][1,4]diazepine as crystals, melting at 74°–76° C.

EXAMPLE 62

A mixture of 5.1 g of 7-hexyl-5-(3-methylphenyl)-1,3-dihydro-2H-thieno[2,3-e]-1,4-diazepin-2-one and 3.7 g of Lawesson reagent in 100 ml of toluene is stirred at 30°–40° C. for an hour. The resultant solution is concentrated under reduced pressure, and the residue is subjected to chromatography on silica gel and then eluted with a mixture of chloroform-methanol (100:1 to 100:2). The eluate of the objective fraction is concentrated under reduced pressure to give 4.7 g of thione compound as crystals.

To a suspension of 4.7 g of thus obtained thione compound in 50 ml of methanol is added 2.2 g of 100% hydrazine hydrate under ice-cooling with stirring and the mixture is stirred for an hour. After the mixture is concentrated under reduced pressure at 30°–40° C., the residue is dissolved in 100 ml of chloroform and the solution is dried over anhydrous magnesium sulfate. After separating by filtration, the filtrate is concentrated under reduced pressure and the residue is dissolved in 100 ml of toluene. To the solution are added 3.2 g of acetic anhydride and 4.8 g of acetic acid, and the mixture is refluxed under heating for 2 hours and then concentrated under reduced pressure. The residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the residue is subjected to chromatography on silica gel and then eluted with a mixture of ethyl acetate-methanol (100:1 to 100:10). The eluate of the objective fraction is concentrated under reduced pressure and the residue is crystallized from a mixture of ethyl acetateisopropyl ether to give 1.5 g of 2-hexyl-4-(3-methylphenyl)-9-methyl-6H-thieno[3,2- f][1,2,4]triazolo[4,3-a][1,4]diazepine as crystals, melting at 57°–59° C.

EXAMPLE 63

A mixture of 5.3 g of 7-hexyl-5-(2,4-dimethylphenyl)-1,3-dihydro-2H-thieno[2,3-e]-1,4-diazepin-2-one and 3.7 g of Lawesson reagent in 100 ml of toluene is stirred at 40°–45° C. for 30 minutes. The resultant solution is concentrated under reduced pressure, and the residue is subjected to chromatography on silica gel and then eluted with a mixture of chloroform-methanol (100:1 to 100:2). The eluate of the objective fraction is concentrated under reduced pressure to give 5.1 g of thione compound as crystals.

To a suspension of 5.1 g of thus obtained thione compound in 50 ml of methanol is added 2.3 g of 100% hydrazine hydrate under ice-cooling with stirring and the mixture is stirred for an hour. After the mixture is concentrated under reduced pressure at 30°–40° C., the residue is dissolved in 100 ml of chloroform and the solution is dried over anhydrous magnesium sulfate. After separating by filtration, the filtrate is concentrated under reduced pressure and the residue is dissolved in 100 ml of toluene. To the solution are added 3.4 g of acetic anhydride and 5 g of acetic acid, and the mixture is refluxed under heating for 2 hours and then concentrated under reduced pressure The residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the residue is subjected to chromatography on silica gel and then eluted with a mixture of ethyl acetate-methanol (100:1 to 100:10). The eluate of the objective fraction is concentrated under reduced pressure and the residue is crystallized from a mixture of ethyl acetate-isopropyl ether to give 2.1 g of 2-hexyl-4-(2,4-dimethylphenyl)-9-methyl-6H-thieno[3,2-f][1,2,4]triazolo[4,3-a][1,4]diazepine as crystals, melting at 99°–101° C.

EXAMPLE 64

A mixture of 4 g of 7-hexyl-5-(2,3-dimethylphenyl)-1,3-dihydro-2H-thieno[2,3-e]-1,4-diazepin-2-one and 2.8 g of Lawesson reagent in 100 ml of toluene is stirred at 40° C. for 30 minutes. The resultant solution is concentrated under reduced pressure, and the residue is subjected to chromatography on silica gel and then eluted with a mixture of chloroform-methanol (100:1 to 100:3). The eluate of the objective fraction is concentrated under reduced pressure to give 3.7 g of thione compound as crystals.

To a suspension of 3.7 g of thus obtained thione compound in 50 ml of methanol is added 1.7 g of 100% hydrazine hydrate under ice-cooling with stirring and the mixture is stirred for an hour. After the mixture is concentrated under reduced pressure at 30°-35° C., the residue is dissolved in 100 ml of chloroform and the solution is dried over anhydrous magnesium sulfate. After separating by filtration, the filtrate is concentrated under reduced pressure and the residue is dissolved in 100 ml of toluene To the solution are added 2.5 g of acetic anhydride and 3.6 g of acetic acid, and the mixture is refluxed under heating for 2 hours and then concentrated under reduced pressure The residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the residue is subjected to chromatography on silica gel and then eluted with a mixture of ethyl acetate-methanol (100:1 to 100:10). The eluate of the objective fraction is concentrated under reduced pressure and the residue is crystallized from a mixture of ethyl acetate-isopropyl ether to give 2.4 g of 2-hexyl-4-(2,3-dimethylphenyl)-9-methyl-6H-thieno[3,2-f][1,2,4]triazolo[4,3-a][1,4]diazepine as crystals, melting at 103°–105° C.

EXAMPLE 65

A mixture of 7 g of 7-hexyl-5-(2,5-dimethylphenyl)-1,3-dihydro-2H-thieno[2,3-e]-1,4-diazepin-2-one and 4.7 g of Lawesson reagent in 100 ml of toluene is stirred at 40° C. for an hour. The resultant solution is concentrated under reduced pressure, and the residue is subjected to chromatography on silica gel and then eluted with a mixture of chloroform-methanol (100:1 to 100:2). The eluate of the objective fraction is concentrated under reduced pressure to give 6 g of thione compound as amorphous powder.

To a suspension of 6 g of thus obtained thione compound in 50 ml of methanol is added 2.5 g of 100% hydrazine hydrate under ice-cooling with stirring and the mixture is stirred for 30 minutes. After the mixture is concentrated under reduced pressure at 30°–40° C., the residue is dissolved in 100 ml of chloroform and the solution is dried over anhydrous magnesium sulfate. After separating by filtration, the filtrate is concentrated under reduced pressure and the residue is dissolved in 100 ml of toluene. To the solution are added 4 g of acetic anhydride and 5.8 g of acetic acid, and the mixture is refluxed under heating for 3 hours and then concentrated under reduced pressure. The residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the resulting oil is subjected to chromatography on silica gel and then eluted with a mixture of ethyl acetate-methanol (100:1 to 100:10). The eluate of the objective fraction is concentrated under reduced pressure and the residue is crystallized from a mixture of ethyl acetate-isopropyl ether to give 0.23 g of 2-hexyl-4-(2,5-dimethylphenyl)-9-methyl-6H-thieno[3,2-f][1,2,4]triazolo[4,3-a][1,4]diazepine as crystals, melting at 81°–84° C.

EXAMPLE 66

A mixture of 5.3 g of 7-hexyl-5-(3,4-dimethylphenyl)-1,3-dihydro-2H-thieno[2,3-e]-1,4-diazepin-2-one and 3.7 g of Lawesson reagent in 100 ml of toluene is stirred at 40° C. for an hour. The resultant solution is concentrated under reduced pressure, and the residue is subjected to chromatography on silica gel and then eluted with a mixture of chloroform-methanol (100:1 to 100:2). The eluate of the objective fraction is concentrated under reduced pressure to give 5.6 g of thione compound as crystals.

To a suspension of 5.6 g of thus obtained thione compound in 50 ml of methanol is added 2.4 g of 100% hydrazine hydrate under ice-cooling with stirring and the mixture is stirred for an hour. After the mixture is concentrated under reduced pressure, the residue is dissolved in 100 ml of chloroform and the solution is dried over anhydrous magnesium sulfate. After separating by filtration, the filtrate is concentrated under reduced pressure and the residue is dissolved in 100 ml of toluene. To the solution are added 3.4 g of acetic anhydride and 5 g of acetic acid, and the mixture is refluxed under heating for 2 hours and then concentrated under reduced pressure The residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the resulting oil is subjected to chromatography on silica gel and then eluted with a mixture of ethyl acetate-methanol (100:1 to 100:10). The eluate of the objective fraction is concentrated under reduced pressure and the residue is crystallized from a mixture of ethyl acetate-isopropyl ether to give 0.33 g of 2-hexyl-4-(3,4-dimethylphenyl)-9-methyl-6H-thieno[3,2-f][1,2,4]triazolo[4,3-a][1,4]diazepine as crystals, melting at 98°-100° C.

EXAMPLE 67

A mixture of 6.2 g of 7-hexyl-5-(3,4,5-trimethoxyphenyl)-1,3-dihydro-2H-thieno[2,3-e]-1,4-diazepin-2-one and 3.7 g of Lawesson reagent in 100 ml of toluene is stirred at 60° C. for 3 hours. The resultant solution is concentrated under reduced pressure, and the residue is subjected to chromatography on silica gel and then eluted with a mixture of chloroform-methanol (100:1 to 100:2). The eluate of the objective fraction is concentrated under reduced pressure to give 5.9 g of thione compound as crystals.

To a suspension of 5.9 g of thus obtained thione compound in 50 ml of methanol is added 2.2 g of 100% hydrazine hydrate under ice-cooling with stirring and the mixture is stirred for an hour. After the mixture is concentrated under reduced pressure, the residue is dissolved in 100 ml of chloroform and the solution is dried over anhydrous magnesium sulfate. After separating by filtration, the filtrate is concentrated under reduced pressure and the residue is dissolved in 100 ml of toluene. To the solution are added 3.4 g of acetic anhydride and 5 g of acetic acid, and the mixture is refluxed under heating for 2 hours and then concentrated under reduced pressure The residue is dissolved in 100 ml of chloroform, and the solution is washed with 5% aqueous sodium hydrogencarbonate solution and sodium chloride solution and dried over anhydrous magnesium sulfate.

After separating by filtration, the filtrate is concentrated under reduced pressure, and the resulting oil is subjected to chromatography on silica gel and then eluted with a mixture of ethyl acetate-methanol (100:1 to 100:10). The eluate of the objective fraction is concentrated under reduced pressure and the residue is crystallized from a mixture of ethyl acetate-isopropyl ether to give 3.97 g of 2-hexyl-4-(3,4,5-trimethoxyphenyl)-9-methyl-6H-thieno[3,2-f][1,2,4]triazolo[4,3-a][1,4]diazepine as crystals, melting at 111°-113° C.

EXAMPLE 68

A suspension of 5.32 g of 7-hexyl-3-methyl-5-(2-methylphenyl)-1,3-dihydro-2H-thieno[2,3-e]-1,4-diazepin-2-one and 2 g of phosphorus pentasulfide in 60 ml of toluene is stirred at 80°-85° C. for 3 hours. The resultant solution is concentrated under reduced pressure, and the residue is dissolved in 200 ml of chloroform. The solution is washed with 5% aqueous sodium hydrogencarbonate solution and sodium chloride solution and dried over anhydrous magnesium sulfate. After separating by filtration, the filtrate is concentrated under reduced pressure and the residue is crystallized from isopropyl ether to give 3.92 g of thione compound.

To a suspension of 3.92 g of thus obtained thione compound in 50 ml of methanol is added 1.58 g of 100% hydrazine hydrate and the mixture is stirred for 1.5 hours. After the mixture is concentrated under reduced pressure, the residue is dissolved in 30 ml of toluene and the solution is dried over anhydrous magnesium sulfate. After separating by filtration, to the toluene solution is added 5.13 g of ethyl orthoacetate and the mixture is refluxed under heating for 2 hours. After cooling, the mixture is washed with 5% aqueous sodium hydrogencarbonate solution and sodium chloride solution, and dried over anhydrous magnesium sulfate. After separating by filtration, the filtrate is concentrated under reduced pressure, and the resulting oil is subjected to chromatography on silica gel and crystallized from a mixture of hexane-isopropyl ether to give 2.82 g of 2-hexyl-4-(2-methylphenyl)- 6,9-dimethyl 6H-thieno[3,2-f][1,2,4]triazolo[4,3-a][1,4]diazepine as colorless crystals, melting at 83°-85° C.

EXAMPLE 69

A mixture of 17.2 g of 7-decyl-5-(2-methoxyphenyl)-1,3-dihydro-2H-thieno[2,3-e]-1,4-diazepin-2-one and 4.2 g of phosphorus pentasulfide in 86 ml of pyridine is stirred at 80°-83° C. for 45 minutes The resultant solution is poured into ice-cold water and extracted with 100 ml of chloroform. The extract is washed with water and dried over anhydrous magnesium sulfate. After separating by filtration, the filtrate is concentrated under reduced pressure to give 24.4 g of thione compound as oil.

To a suspension of 24.4 g of the thione compound in 80 ml of methanol is added 6.9 g of 100% hydrazine hydrate under ice-cooling with stirring and stirred for an hour. The mixture is concentrated under reduced pressure at a low temperature and the residue is dissolved in 100 ml of chloroform. The solution is washed with ice-cold water and dried over anhydrous magnesium sulfate. After separating by filtration, the filtrate is concentrated under reduced pressure and the residue is dissolved in 40 ml of toluene. To the solution are added 1.5 g of acetic anhydride and 1.2 g of acetic acid and the mixture is refluxed under heating for 1.5 hours. After the mixture is concentrated under reduced pressure, the residue is dissolved in 100 ml of chloroform, and the solution is washed with 5% aqueous sodium hydrogencarbonate solution and sodium chloride solution, and dried over anhydrous magnesium sulfate. After separating by filtration, the filtrate is concentrated under reduced pressure, and the residue is crystallized from isopropyl ether to give 3.3 g of 2-decyl-4-(2-methoxyphenyl)-9-methyl-6H-thieno[3,2-f][1,2,4]triazolo[4,3-a][1,4]diazepine as crystals, melting at 90°-92° C.

EXAMPLE 70

A mixture of 7.9 g of 7-decyl-5-(2-methylphenyl)-1,3-dihydro-2H-thieno[2,3-e]-1,4-diazepin-2-one and 2 g of phosphorus pentasulfide in 50 ml of pyridine is stirred at 80°-83° C. for 5 hours. The resultant solution is poured into ice-cold water and the precipitated crystals are collected by filtration. The resulting crude thione compound is subjected to chromatography on silica gel to give 3 g of thione compound as crystals, melting at 161°–163° C.

To a suspension of 3 g of the thione compound in 100 ml of methanol is added 1.3 g of 100% hydrazine hydrate under ice-cooling with stirring and stirred for 30 minutes. Then, the resultant solution is concentrated under reduced pressure at a low temperature, the residue is dissolved in 50 ml of chloroform and the solution is dried over anhydrous magnesium sulfate. After separating by filtration, the filtrate is concentrated under reduced pressure. To a solution of the residue in 50 ml of toluene are added 0.9 g of acetic anhydride and 2.6 g of acetic acid and the mixture is refluxed under heating for 2.5 hours. After the mixture is concentrated under reduced pressure, the residue is dissolved in 50 ml of chloroform, and the solution is washed with 5% aqueous sodium hydrogencarbonate solution and sodium chloride solution, and dried over anhydrous magnesium sulfate. After separating by filtration, the filtrate is concentrated under reduced pressure, and the resulting oil is subjected to chromatography on silica gel and eluted with a mixture of chloroform-methanol (100:1 to 100:3). The eluate of the objective fraction is concentrated under reduced pressure and the residue is crystallized from petroleum ether to give 1.1 g of 2-decyl-4-(2-methylphenyl)-9-methyl-6H-thieno[3,2-f][1,2,4]triazolo[4,3-a][1,4]diazepine as crystals, melting at 61°–63° C.

EXAMPLE 71

A mixture of 7 g of 5-(2-chlorophenyl)-7-hexadecyl-1,3-dihydro-2H-thieno[2,3-e]-1,4-diazepin-2-one and 1.4 g of phosphorus pentasulfide in 50 ml of pyridine is stirred at 80°–83° C. for 8 hours. The resultant solution is poured into ice-cold water and extracted with 200 ml of ethyl acetate. The extract is washed with 5% hydrochloric acid solution and sodium chloride solution and dried over anhydrous magnesium sulfate. After separating by filtration, the filtrate is concentrated under reduced pressure and the residue is subjected to chromatography on silica gel to give 3 g of thione compound as oil.

To a suspension of 3 g of the thione compound in 50 ml of methanol is added 1 g of 100% hydrazine hydrate under ice-cooling with stirring and stirred for 40 minutes. The mixture is concentrated under reduced pressure at a low temperature, and the residue is dissolved in 50 ml of chloroform and the solution is dried over anhydrous magnesium sulfate. After separating by filtration, the filtrate is concentrated under reduced pressure and the residue is dissolved in 100 ml of toluene. To the solution are added 0.9 g of acetic anhydride and 2.1 g of acetic acid and the mixture is refluxed under heating for 2 hours. The mixture is concentrated under reduced pressure, and the residue is dissolved in 50 ml of chloroform, and the solution is washed with 5% aqueous sodium hydrogencarbonate solution and sodium chloride solution, and then dried over anhydrous magnesium sulfate. After separating by filtration, the filtrate is concentrated under reduced pressure, and the resulting oil is subjected to chromatography on silica gel and eluted with a mixture of chloroform-methanol (100:1 to 100:3). The eluate of the objective fraction is concentrated under reduced pressure and the residue is crystallized from petroleum ether to give 0.55 g of 4-(2-chlorophenyl)-2-hexadecyl-9-methyl-6H-thieno[3,2-f][1,2,4]-triazolo[4,3-a][1,4]diazepine as crystals, melting at 58°–60° C.

EXAMPLE 72

A mixture of 23 g of 5-(2-chlorophenyl)-2-decyl-1,3-dihydro-2H-thieno[2,3-e]-1,4-diazepin-2-one and 5.5 g of phosphorus pentasulfide in 140 ml of pyridine is stirred at 80°–90° C. for 3 hours. The resultant solution is poured into ice-cold water and extracted with 300 ml of chloroform. The extract is washed with sodium chloride solution and dried over anhydrous magnesium sulfate. After separating by filtration, the filtrate is concentrated under reduced pressure to give 20 g of thione compound as oil.

To a suspension of 18.5 g of the thione compound in 100 ml of methanol is added 7 g of 100% hydrazine hydrate under ice-cooling with stirring and stirred for 30 minutes. The resultant solution is concentrated under reduced pressure at a low temperature, and the residue is dissolved in 100 ml of chloroform. The solution is washed with ice-cold water and dried over anhydrous magnesium sulfate. After separating by filtration, the filtrate is concentrated under reduced pressure. To a solution of the residue in 100 ml of toluene are added 5.2 g of acetic anhydride and 15 g of acetic acid and the mixture is refluxed under heating for 3 hours. After the reaction, the mixture is concentrated under reduced pressure, the residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure. The residue is subjected to chromatography on silica gel and eluted with a mixture of chloroform-methanol (100:1 to 100:3). The eluate of the objective fraction is concentrated under reduced pressure to give 4 g of 4-(2-chlorophenyl)-2-decyl-9-methyl 6H-thieno[3,2-f][1,2,4]triazolo[4,3-a][1,4]-diazepine as oil.

EXAMPLE 73

A mixture of 6.4 g of 5-(2-chlorophenyl)-7-dodecyl-1,3-dihydro-2H-thieno[2,3-e]-1,4-diazepin-2-one and 1.5 g of phosphorus pentasulfide in 50 ml of pyridine is stirred at 83°–85° C. for 3 hours. The resultant solution is poured into ice-cold water with stirring and the precipitated crystals are collected by filtration. The crystals are washed with water and dried to give 6.5 g of thione compound.

To a suspension of 6.5 g of the thione compound in 100 ml of methanol is added 2.4 g of 100% hydrazine hydrate under ice-cooling with stirring and the mixture is stirred for an hour. The resultant solution is concentrated under reduced pressure at a low temperature, the residue is dissolved in 100 ml of chloroform and the solution is dried over anhydrous magnesium sulfate. After separating by filtration, the residue is dissolved in 100 ml of toluene and to the solution are added 1.8 g of acetic anhydride and 5.2 g of acetic acid and then the mixture is refluxed under heating for 2 hours. After the mixture is concentrated under reduced pressure, the residue is dissolved in 100 ml of chloroform, and the solution is washed with 5% aqueous sodium hydrogencarbonate solution and sodium chloride solution and dried over anhydrous magnesium sulfate. After separating by filtration, the filtrate is concentrated under reduced pressure, and the residue is subjected to chromatography on silica gel and eluted with a mixture of chloroform-methanol (100:1 to 100:3). The eluate of the objective fraction is concentrated under reduced pressure to give 4 g of 4-(2-chlorophenyl)-2-dodecyl-9-methyl-6H-thieno[3,2-f][1,2,4]triazolo[4,3-a][1,4]-diazepine as oil.

The following compounds can be prepared in a similar manner as the above Examples.

(74) 4-(2-chlorophenyl)-2-hexyl-6,9-dimethyl-6H-thieno[3,2-f][1,2,4]triazolo[4,3-a][1,4]diazepine, melting at 108°–110° C.
(75) 2-hexyl-4-(2-methoxyphenyl)-6,9-dimethyl-6H-thieno[3,2-f][1,2,4]triazolo[4,3-a][1,4]diazepine, melting at 92°–95° C.
(76) 4-(2-methylphenyl)-9-methyl-2-octyl-6H-thieno[3,2-f][1,2,4]triazolo[4,3-a][1,4]diazepine
(77) 4-(3-methylphenyl)-9-methyl-2-octyl-6H-thieno[3,2-f][1,2,4]triazolo[4,3-a][1,4]diazepine
(78) 4-(4-methylphenyl)-9-methyl-2-octyl-6H-thieno[3,2-f][1,2,4]triazolo[4,3-a][1,4]diazepine
(79) 4-(2,3-dimethylphenyl)-9-methyl-2-octyl-6H-thieno[3,2-f][1,2,4]triazolo[4,3-a][1,4]diazepine
(80) 4-(3,4-dimethylphenyl)-9-methyl-2-octyl-6H-thieno[3,2-f][1,2,4]triazolo[4,3-a][1,4]diazepine
(81) 4-(2,4-dimethylphenyl)-9-methyl-2-octyl-6H-thieno[3,2-f][1,2,4]triazolo[4,3-a][1,4]diazepine
(82) 4-(3,4,5-trimethoxyphenyl)-9-methyl-2-octyl-6H-thieno[3,2-f][1,2,4]triazolo[4,3-a][1,4]diazepine
(83) 2-heptyl-4-(2,3-dimethylphenyl)-9-methyl-6H-thieno[3,2-f][1,2,4]triazolo[4,3-a][1,4]diazepine
(84) 2-heptyl-4-(2-methylphenyl)-9-methyl-6H-thieno[3,2-f][1,2,4]triazolo[4,3-a][1,4]diazepine
(85) 2-hexyl-4-(2,3-dimethoxyphenyl)-9-methyl-6H-thieno[3,2-f][1,2,4]triazolo[4,3-a][1,4]diazepine
(86) 4-(2,3-dimethoxyphenyl)-9-methyl-2-octyl-6H-thieno[3,2-f][1,2,4]triazolo[4,3-a][1,4]diazepine
(87) 2-hexyl-4-(3,4-dimethoxyphenyl)-9-methyl-6H-thieno[3,2-f][1,2,4]triazolo[4,3-a][1,4]diazepine
(88) 4-(3,4-dimethoxyphenyl)-9-methyl-2-octyl-6H-thieno[3,2-f][1,2,4]triazolo[4,3-a][1,4]diazepine
(89) 4-(3-chlorophenyl)-2-hexyl-9-methyl-6H-thieno[3,2-f][1,2,4]triazolo[4,3-a][1,4]diazepine
(90) 4-(4-chlorophenyl)-2-hexyl-9-methyl-6H-thieno[3,2-f][1,2,4]triazolo[4,3-a][1,4]diazepine
(91) 4-(3,4-dichlorophenyl)-2-hexyl-9-methyl-6H-thieno[3,2-f][1,2,4]triazolo[4,3-a][1,4]diazepine
(92) 4-(3,4-dichlorophenyl)-9-methyl-2-octyl-6H-thieno[3,2-f][1,2,4]triazolo[4,3-a][1,4]diazepine
(93) 4-(2,3-dichlorophenyl)-2-hexyl-9-methyl-6H-thieno[3,2-f][1,2,4]triazolo[4,3-a][1,4]diazepine
(94) 4-(2-bromophenyl)-2-hexyl-9-methyl-6H-thieno[3,2-f][1,2,4]triazolo[4,3-a][1,4]diazepine
(95) 4-(2-bromophenyl)-9-methyl-2-octyl-6H-thieno[3,2-f][1,2,4]triazolo[4,3-a][1,4]diazepine
(96) 2-hexyl-4-(2-methylphenyl)-3,6,9-trimethyl-6H-thieno[3,2-f][1,2,4]triazolo[4,3-a][1,4]diazepine
(97) 9-ethyl-2-hexyl-4-(2-methylphenyl)-6H-thieno[3,2-f][1,2,4]triazolo[4,3-a][1,4]diazepine
(98) 2-hexyl-4-(2-methylphenyl)-9-propyl-6H-thieno[3,2-f][1,2,4]triazolo[4,3-a][1,4]diazepine
(99) 2-hexyl-9-methyl-4-(3,4-methylenedioxyphenyl)-6H-thieno[3,2-f][1,2,4]triazolo[4,3-a][1,4]diazepine
(100) 2-hexyl-9-methyl-4-(2-pyridyl)-6H-thieno[3,2-f][1,2,4]triazolo[4,3-a][1,4]diazepine
(101) 2-hexyl-9-methyl-4-(3-pyridyl)-6H-thieno[3,2-f][1,2,4]triazolo[4,3-a][1,4]diazepine
(102) 2-hexyl-9-methyl-4-(4-pyridyl)-6H-thieno[3,2-f][1,2,4]triazolo[4,3-a][1,4]diazepine
(103) 2-hexyl-4-(3,4,5-trimethoxyphenyl)-6,9-dimethyl-6H-thieno[3,2-f][1,2,4]triazolo[4,3-a][1,4]diazepine
(104) 9-ethyl-2-hexyl-4-(3,4,5-trimethoxyphenyl)-6H-thieno[3,2-f][1,2,4]triazolo[4,3-a][1,4]diazepine
(105) 2-hexyl-4-(3,4,5-trimethoxyphenyl)-9-propyl-6H-thieno[3,2-f][1,2,4]triazolo[4,3-a][1,4]diazepine
(106) 2-heptyl-4-(3,4,5-trimethoxyphenyl)-9-methyl-6H-thieno[3,2-f][1,2,4]triazolo[4,3-a][1,4]diazepine
(107) 2-decyl-4-(4-methylphenyl)-9-methyl-6H-thieno[3,2-f][1,2,4]triazolo[4,3-a][1,4]diazepine
(108) 2-decyl-4-(4-methoxyphenyl)-9-methyl-6H-thieno[3,2-f][1,2,4]triazolo[4,3-a][1,4]diazepine
(109) 2-decyl-4-(3-methylphenyl)-9-methyl-6H-thieno[3,2-f][1,2,4]triazolo[4,3-a][1,4]diazepine
(110) 2-decyl-4-(2,3-dimethylphenyl)-9-methyl-6H-thieno[3,2-f][1,2,4]triazolo[4,3-a][1,4]diazepine
(111) 2-decyl-4-(3,4,5-trimethoxyphenyl)-9-methyl-6H-thieno[3,2-f][1,2,4]triazolo[4,3-a][1,4]diazepine
(112) 2-decyl-4-(2,6-dimethoxyphenyl)-9-methyl-6H-thieno[3,2-f][1,2,4]triazolo[4,3-a][1,4]diazepine
(113) 4-(3,4-dichlorophenyl)-2-decyl-9-methyl-6H-thieno[3,2-f][1,2,4]triazolo[4,3-a][1,4]diazepine
(114) 2-dodecyl-4-(4-methylphenyl)-9-methyl-6H-thieno[3,2-f][1,2,4]triazolo[4,3-a][1,4]diazepine
(115) 4-(2-chlorophenyl)-2-hexadecyl-9-methyl-6H-thieno[3,2-f][1,2,4]triazolo[4,3-a][1,4]diazepine
(116) 4-(2-chlorophenyl)-9-methyl-2-octadecyl-6H-thieno[3,2-f][1,2,4]triazolo[4,3-a][1,4]diazepine
(117) 4-(4-chlorophenyl)-2-decyl-9-methyl-6H-thieno[3,2-f][1,2,4]triazolo[4,3-a][1,4]diazepine
(118) 4-(2,6-dichlorophenyl)-2-decyl-9-methyl-6H-thieno[3,2-f][1,2,4]triazolo[4,3-a][1,4]diazepine The followings are pharmaceutical formulation examples which are used as drugs containing the compound of the present invention:

Formulation example 1: Tablets

A composition of 1 part of the compound (I), 30 parts of lactose, 40 parts of crystalline cellulose and 5 parts of corn starch is mixed well, and kneaded with binder prepared by 2 parts of corn starch. The paste is passed through a 16 mesh sieve and dried in an oven at 50° C. and forced through a 24 mesh sieve. The powder thus obtained, 10 parts of corn starch, 13 parts of crystalline cellulose and 9 parts of talc are mixed well and the mixture was compressed with a punch into tablets containing 110 mg of active ingredient.

Formulation example 2: 1% Powder

A composition of 1 part of the compound (I) and 90 parts of lactose is mixed well and kneaded with binder prepared by a suitable amount of methylcellulose. The mixture was passed through a 16 mesh sieve and dried in an oven at 50° C. The dried granules were forced through 32 mesh sieve with pressure and mixed with a suitable amount of silicon dioxide to produce 1% powder.

Although the present invention has been adequately discussed in the foregoing specification and examples included therein, one readily recognizes that various changes and modifications may be made without departing from the spirit and scope of the present invention

We claim:
1. A thienotriazolodiazepine compound of the formula:

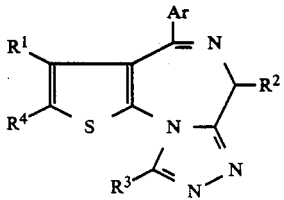

wherein Ar is phenyl, pyridyl, substituted phenyl or substituted pyridyl; $R^1$ and $R^3$ are the same or different and each is hydrogen, alkyl having 1 to 4 carbon atoms; $R^2$ is hydrogen, alkyl having 1 to 4 carbon atoms or trifluoromethyl; $R^4$ is straight or branched chain alkyl, alkenyl or alkynyl having 6 to 18 carbon atoms, or a pharmaceutically acceptable acid addition salt thereof.

2. A compound of claim 1 selected from the group consisting of 4-(2-chlorophenyl)-2-hexyl-9-methyl-6H-thieno[3,2-f][1,2,4]triazolo[4,3-a][1,4]diazepine, 2-hexyl-4-(2-methylphenyl)-9-methyl-6H-thieno[3,2-f][1,2,4]triazolo[4,3-a][1,4]diazepine, 2-hexyl-4-(2-methoxyphenyl)-9-methyl-6H-thieno[3,2-f][1,2,4]triazolo[4,3-a][1,4]diazepine, 4-(2-chlorophenyl)-2-octyl-9-methyl-6H-thieno[3,2-f][1,2,4]triazolo[4,3-a][1,4]diazepine, 2-hexyl-4-(4-methylphenyl)-9-methyl-6H-thieno[3,2-f][1,2,4]triazolo[4,3-a][1,4]diazepine, 2-hexyl-4-(3-methylphenyl)-9-methyl-6H-thieno[3,2-f][1,2,4]triazolo[4,3-a][1,4]diazepine, 2-hexyl-4-(3,4,5-trimethoxyphenyl)-9-methyl-6H-thieno[3,2-f][1,2,4]triazolo[4,3-a][1,4]diazepine, 2-hexyl-4-(2,5-dimethylphenyl)-9-methyl-6H-thieno[3,2-f][1,2,4]triazolo [4,3-a][1,4]diazepine, 4-(2-chlorophenyl)-2-hexyl-6,9-dimethyl-6H-thieno[3,2-f][1,2,4]triazolo [4,3-a][1,4]diazepine, 2-hexyl-4-(2-methoxyphenyl)-6,9-dimethyl-6H-thieno[3,2-f][1,2,4]triazolo[4,3-a][1,4]diazepine and 2-hexyl-4-(2-methylphenyl)-6,9-dimethyl-6H-thieno[3,2-f][1,2,4]triazolo [4,3-a][1,4]diazepine.

3. A drug for treatment of circulatory diseases comprising a compound of claim 1 or 2 or a pharmaceutically acceptable acid addition salt thereof as an active ingredient.

4. A drug of claim 3 for treatment of circulatory diseases which is a coronary vasodilating agent, a drug for heart failure or a cerebral vasodilating agent.

5. A drug for treatment of various diseases induced by platelet activating factor comprising a compound of claim 1 or 2 or a pharmaceutically acceptable acid addition salt thereof as an active ingredient.

* * * * *